(12) United States Patent
McGahan et al.

(10) Patent No.: US 8,206,397 B2
(45) Date of Patent: Jun. 26, 2012

(54) INSTRUMENTS AND TECHNIQUES FOR DISC SPACE PREPARATION

(75) Inventors: Thomas V. McGahan, Germantown, TN (US); Steven D. DeRidder, Bartlett, TN (US); Eric C. Lange, Germantown, TN (US)

(73) Assignee: Warsaw Orthopedic, Warsaw, IN (US)

( * ) Notice: Subject to any disclaimer, the term of this patent is extended or adjusted under 35 U.S.C. 154(b) by 1477 days.

(21) Appl. No.: 11/409,901

(22) Filed: Apr. 24, 2006

(65) Prior Publication Data

US 2006/0195109 A1 Aug. 31, 2006

Related U.S. Application Data

(60) Division of application No. 10/219,040, filed on Aug. 14, 2002, now Pat. No. 7,033,362, which is a continuation of application No. PCT/US01/05500, filed on Feb. 22, 2001.

(60) Provisional application No. 60/184,107, filed on Feb. 22, 2000.

(51) Int. Cl.
*A61B 17/16* (2006.01)
(52) U.S. Cl. .......................................... 606/90
(58) Field of Classification Search ................ 606/86 A, 606/86 R, 79–85, 90, 99, 100, 105; 623/17.11–17.16
See application file for complete search history.

(56) References Cited

U.S. PATENT DOCUMENTS

| | | | |
|---|---|---|---|
| 4,586,496 A | 5/1986 | Keller | |
| 4,697,586 A | 10/1987 | Gazale | |
| 5,484,446 A | 1/1996 | Burke et al. | |
| 5,486,180 A | 1/1996 | Dietz et al. | |
| 5,571,109 A | 11/1996 | Bertagnoli | |
| 5,688,281 A | 11/1997 | Cripe et al. | |
| 5,772,661 A | 6/1998 | Michelson | |
| 5,803,904 A | 9/1998 | Mehdizadeh | |
| 6,030,390 A * | 2/2000 | Mehdizadeh | 606/84 |
| 6,042,582 A * | 3/2000 | Ray | 606/86 A |
| 6,159,214 A * | 12/2000 | Michelson | 606/80 |
| 6,210,412 B1 * | 4/2001 | Michelson | 606/86 A |
| 6,224,599 B1 * | 5/2001 | Baynham et al. | 606/90 |
| 6,428,541 B1 * | 8/2002 | Boyd et al. | 606/86 A |
| 6,436,098 B1 * | 8/2002 | Michelson | 606/86 A |
| 6,589,247 B2 * | 7/2003 | McGahan et al. | 606/90 |
| 6,595,995 B2 * | 7/2003 | Zdeblick et al. | 606/80 |
| 6,599,294 B2 * | 7/2003 | Fuss et al. | 606/99 |
| 6,712,825 B2 * | 3/2004 | Aebi et al. | 606/90 |
| 6,716,218 B2 * | 4/2004 | Holmes et al. | 606/105 |
| 6,755,841 B2 * | 6/2004 | Fraser et al. | 606/99 |
| 6,761,723 B2 * | 7/2004 | Buttermann et al. | 606/79 |
| 7,014,617 B2 * | 3/2006 | Grinberg | 600/587 |

(Continued)

FOREIGN PATENT DOCUMENTS

WO WO 98 04202 A 2/1989

(Continued)

*Primary Examiner* — Thomas C. Barrett
*Assistant Examiner* — Christopher Beccia

(57) ABSTRACT

A series of instruments (30, 80, 120, 210, 510, 550) are provided for direct-anterior and oblique-anterior disc space and end plate preparation. The instruments (30, 80, 120, 210, 510, 550) provide precise guidance for channel formation in the vertebral endplates by guiding rotating and bladed cutting instruments (122, 250, 580). Instrumentation (550) for oblique-anterior disc space preparation includes compound angulation to account for the angle of approach to the spine and the angulation between adjacent vertebrae. Methods and techniques for use of the instruments (30, 80, 120, 210, 510, 550) are also described.

13 Claims, 41 Drawing Sheets

23E

U.S. PATENT DOCUMENTS

| | | | |
|---|---|---|---|
| 7,081,118 B2 * | 7/2006 | Weber et al. | 606/90 |
| 7,108,698 B2 * | 9/2006 | Robbins et al. | 606/90 |
| 7,153,304 B2 * | 12/2006 | Robie et al. | 606/90 |
| 7,169,152 B2 * | 1/2007 | Foley et al. | 606/90 |
| 7,189,234 B2 * | 3/2007 | Zucherman et al. | 606/249 |
| 2001/0034526 A1 * | 10/2001 | Kuslich et al. | 606/80 |

FOREIGN PATENT DOCUMENTS

| | | |
|---|---|---|
| WO | WO 99 52446 A | 10/1999 |
| WO | WO 99 52453 A | 10/1999 |
| WO | WO 01 28435 A | 4/2001 |

* cited by examiner

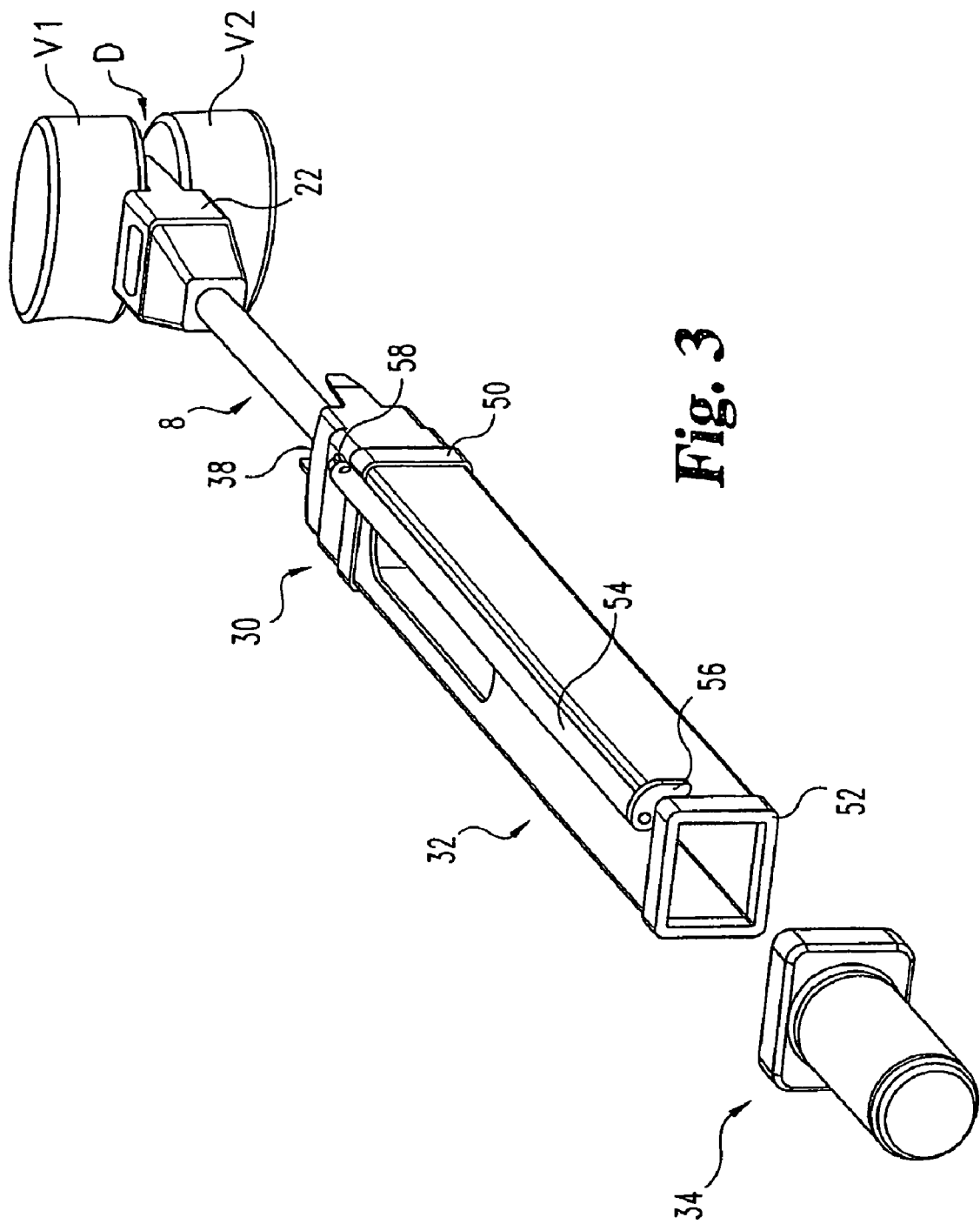

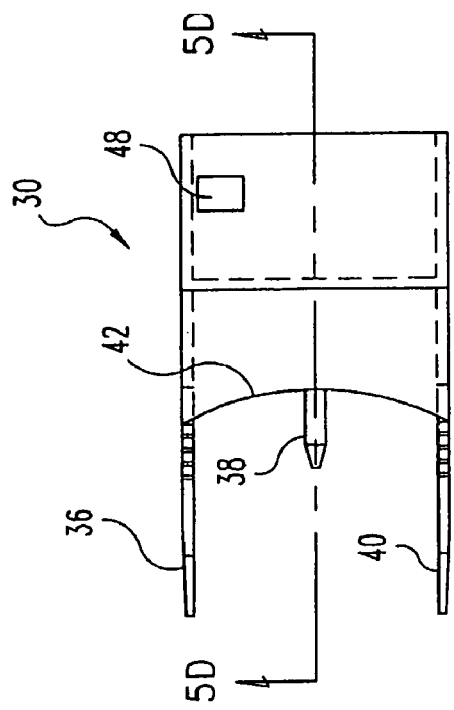
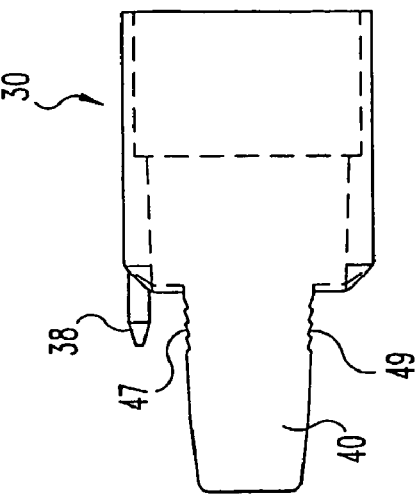
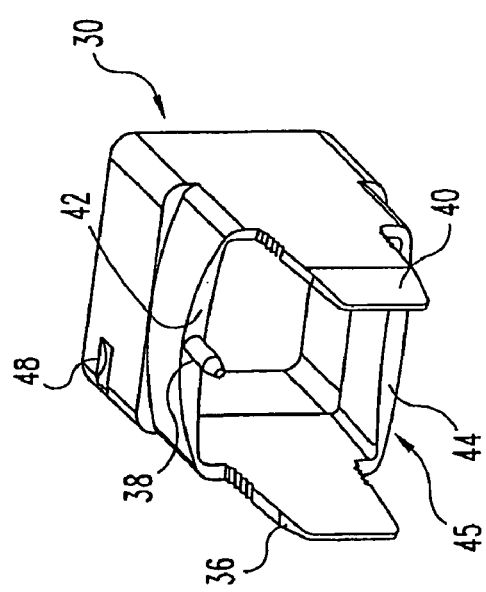

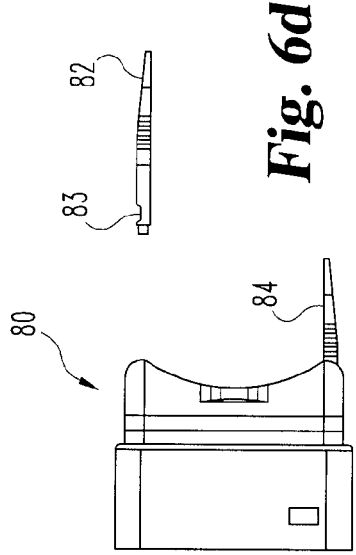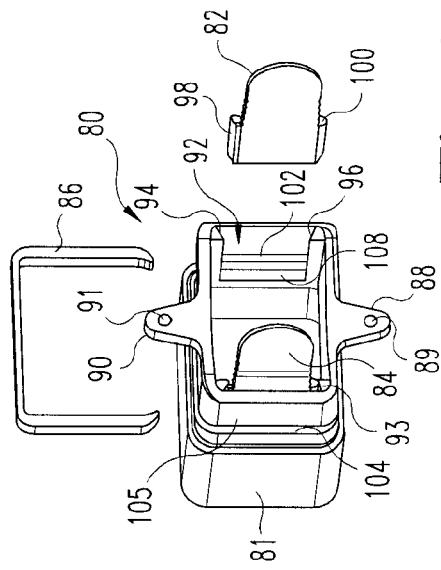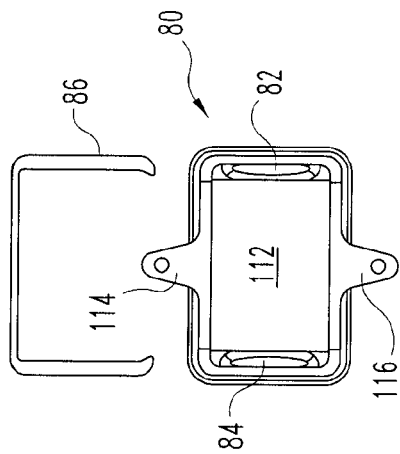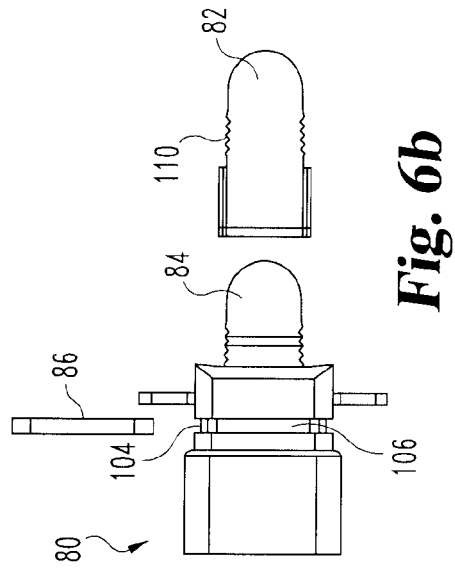

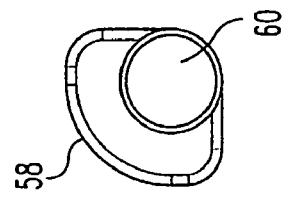
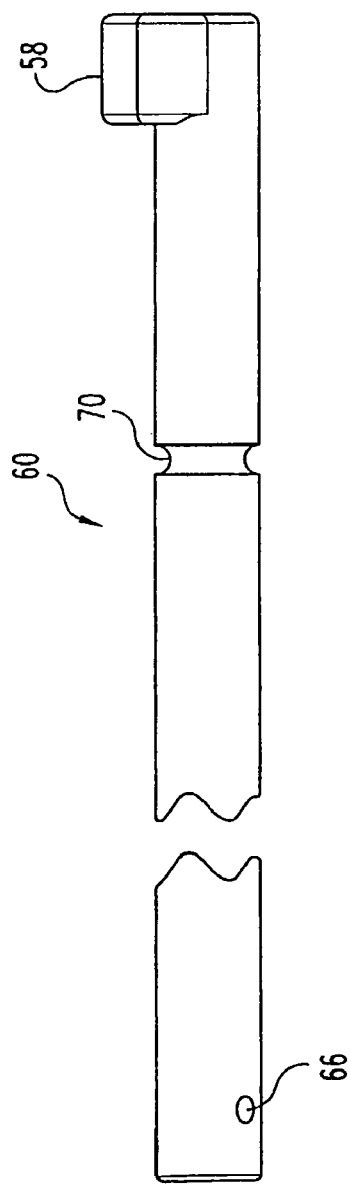
Fig. 7b
Fig. 7a

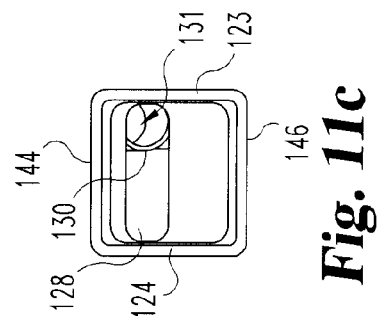
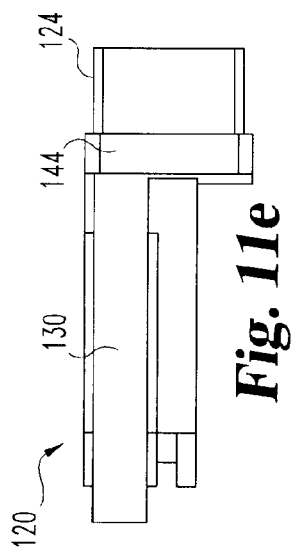
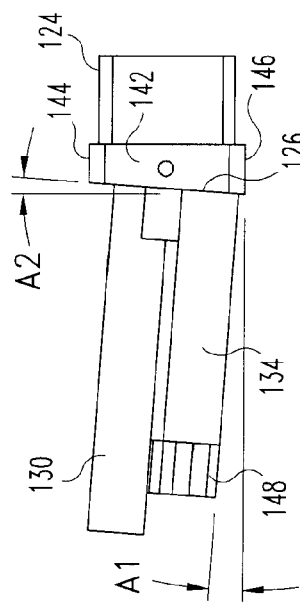
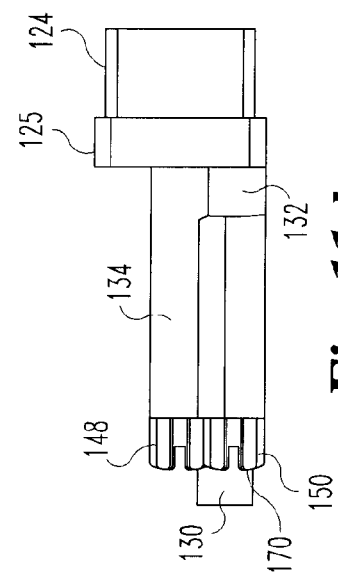
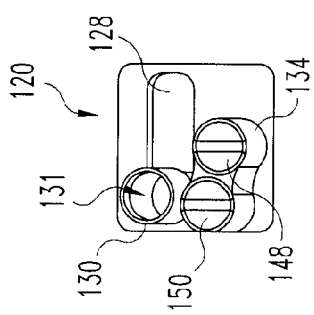

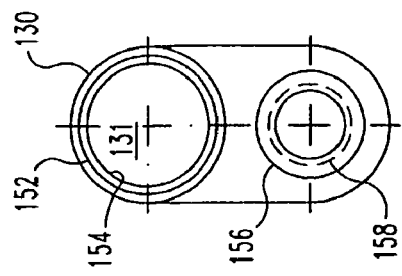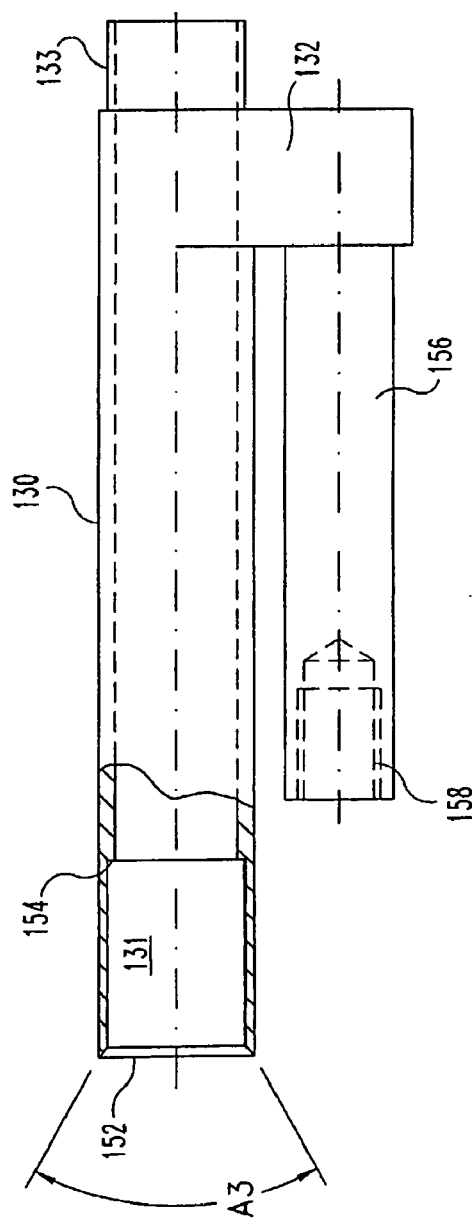
Fig. 12b
Fig. 12a

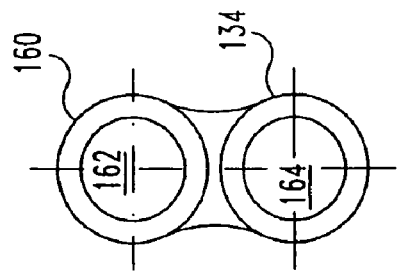
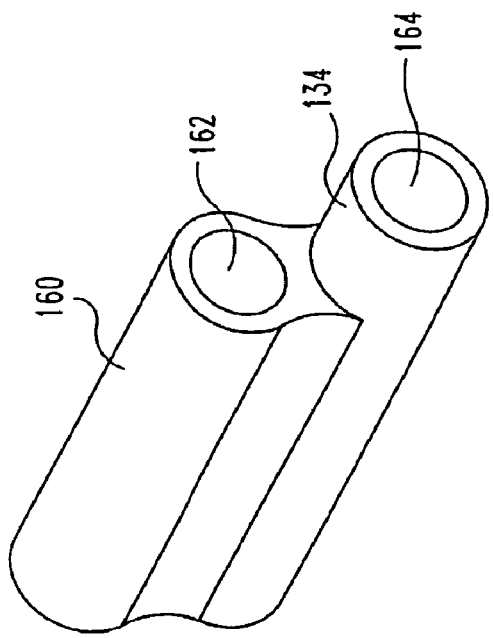
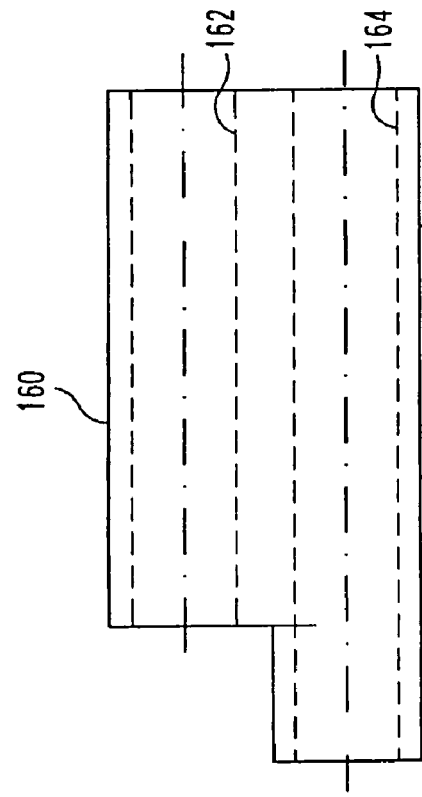
*Fig. 13a*
*Fig. 13b*
*Fig. 13c*

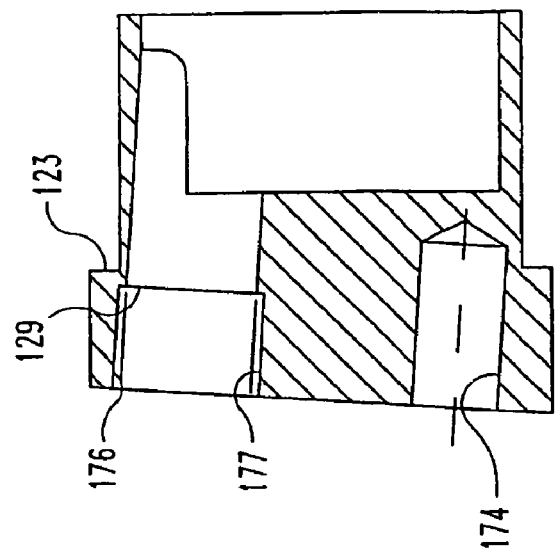
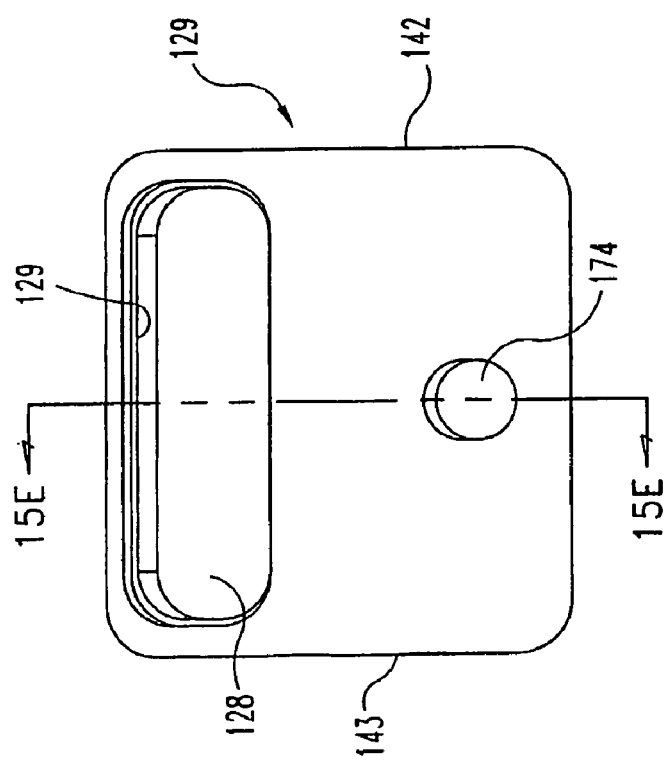

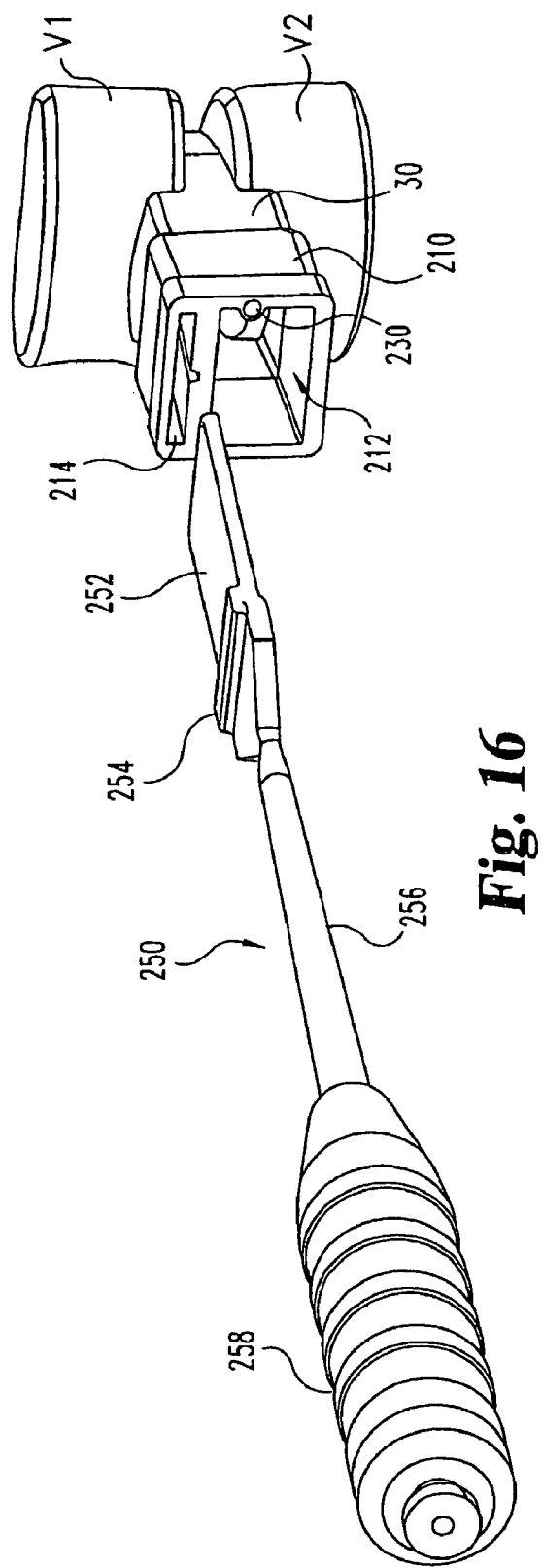

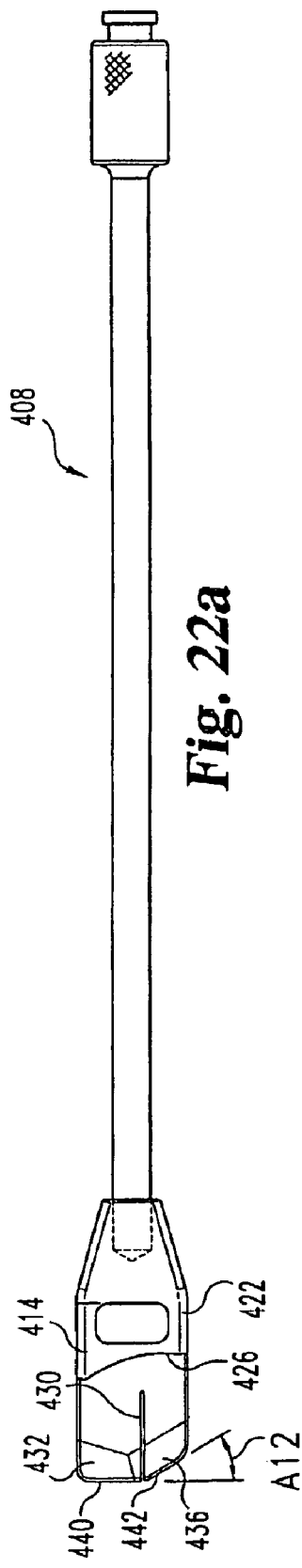
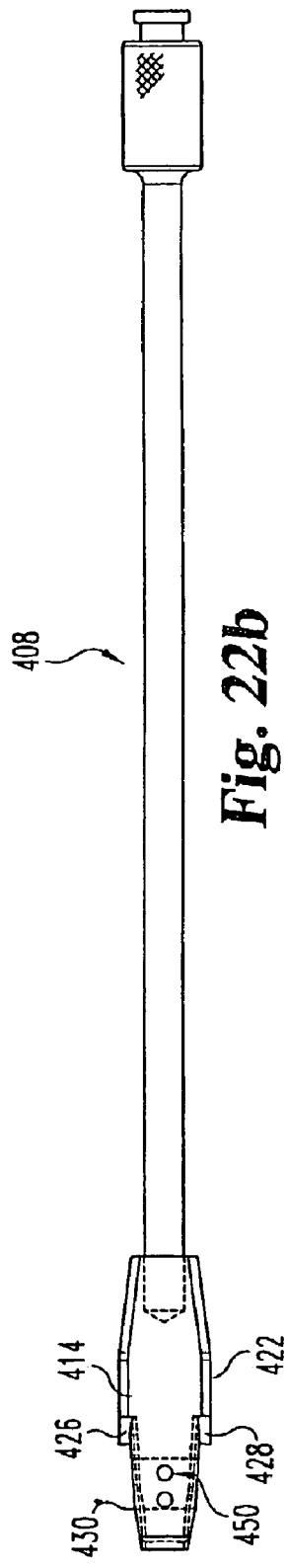
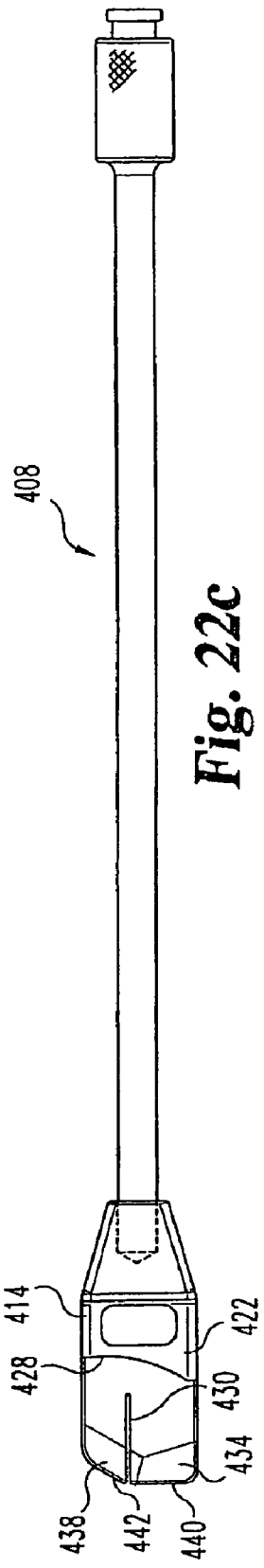
Fig. 22a
Fig. 22b
Fig. 22c

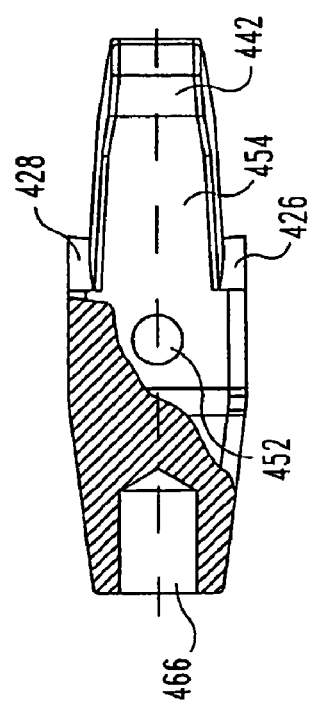
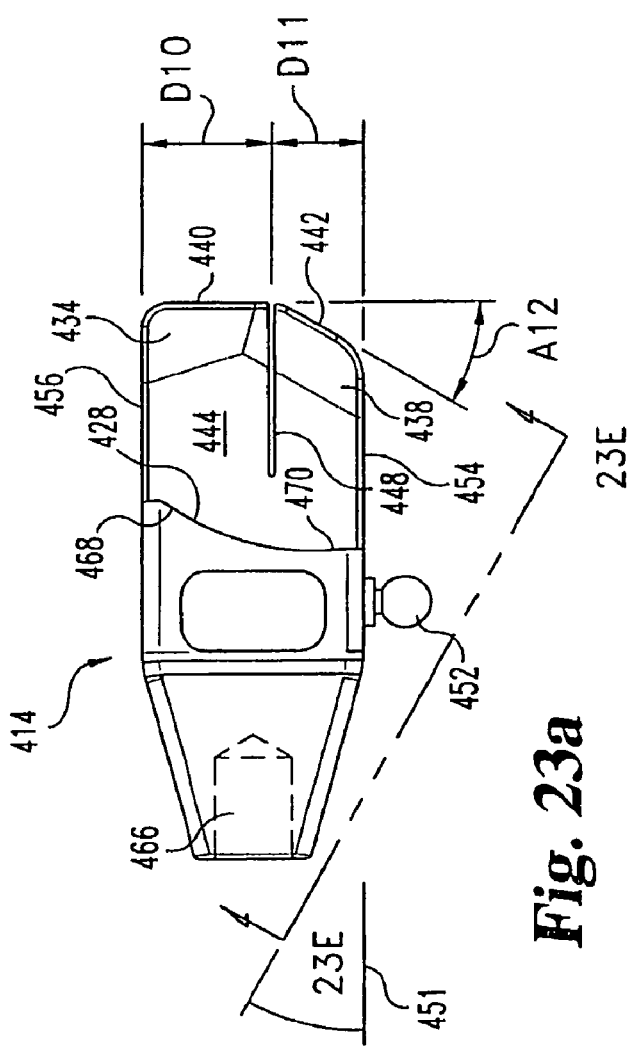
Fig. 23a
Fig. 23b

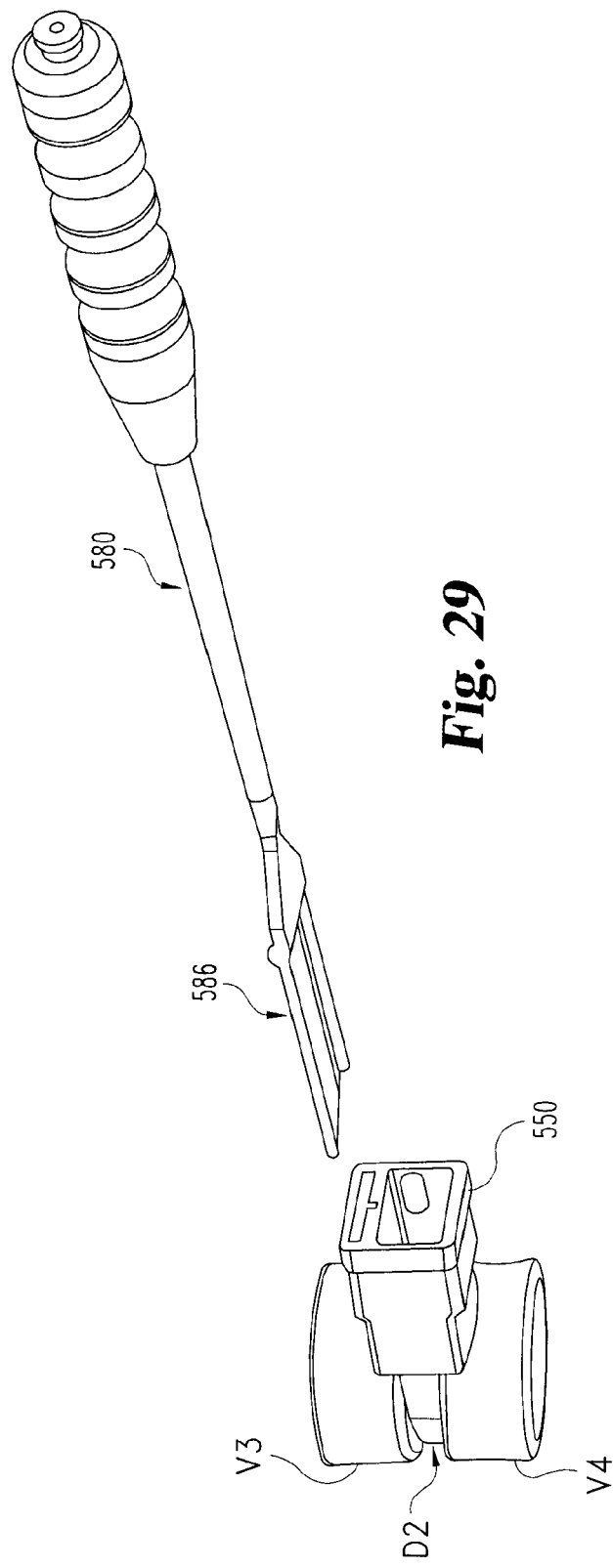

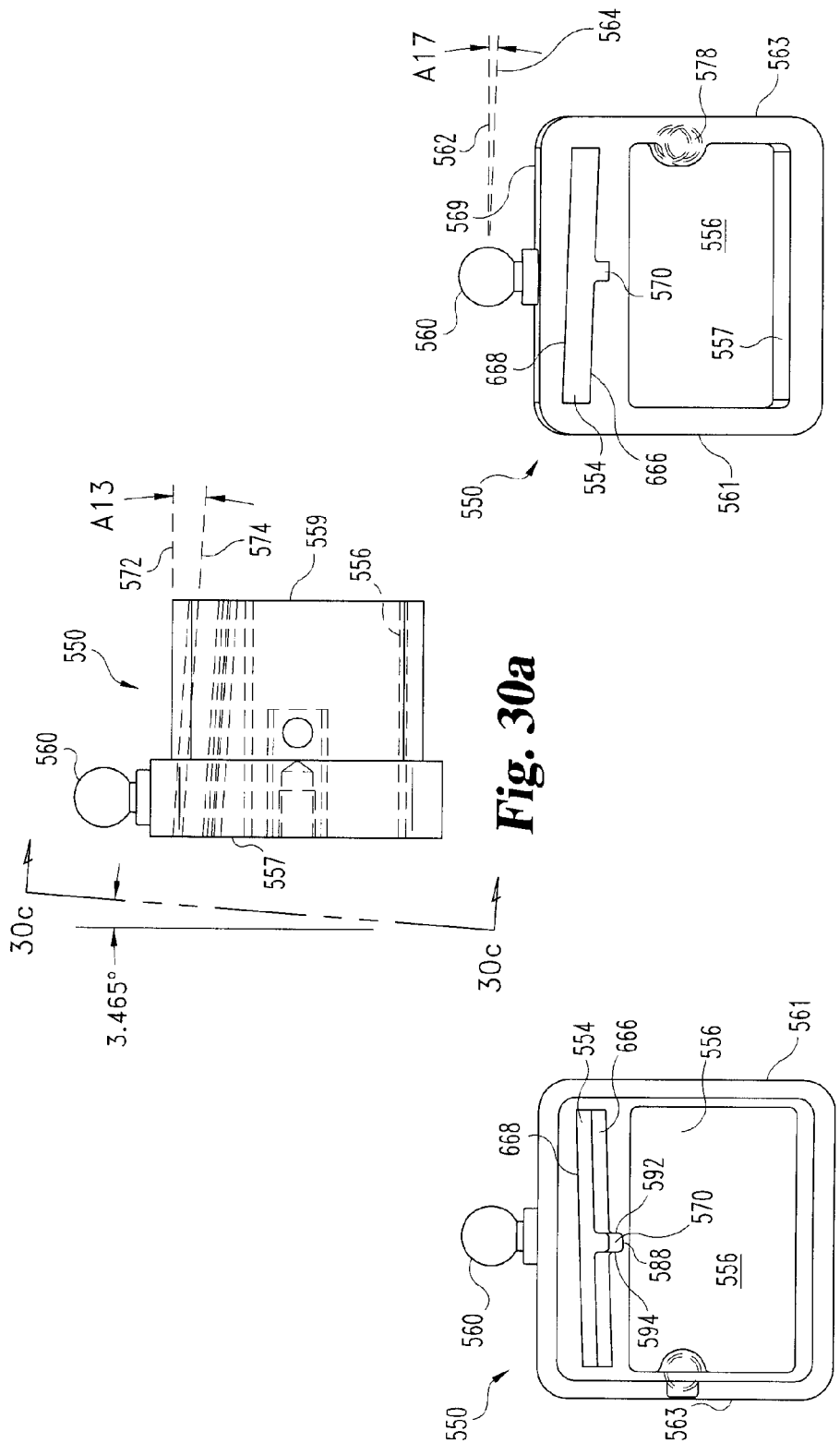

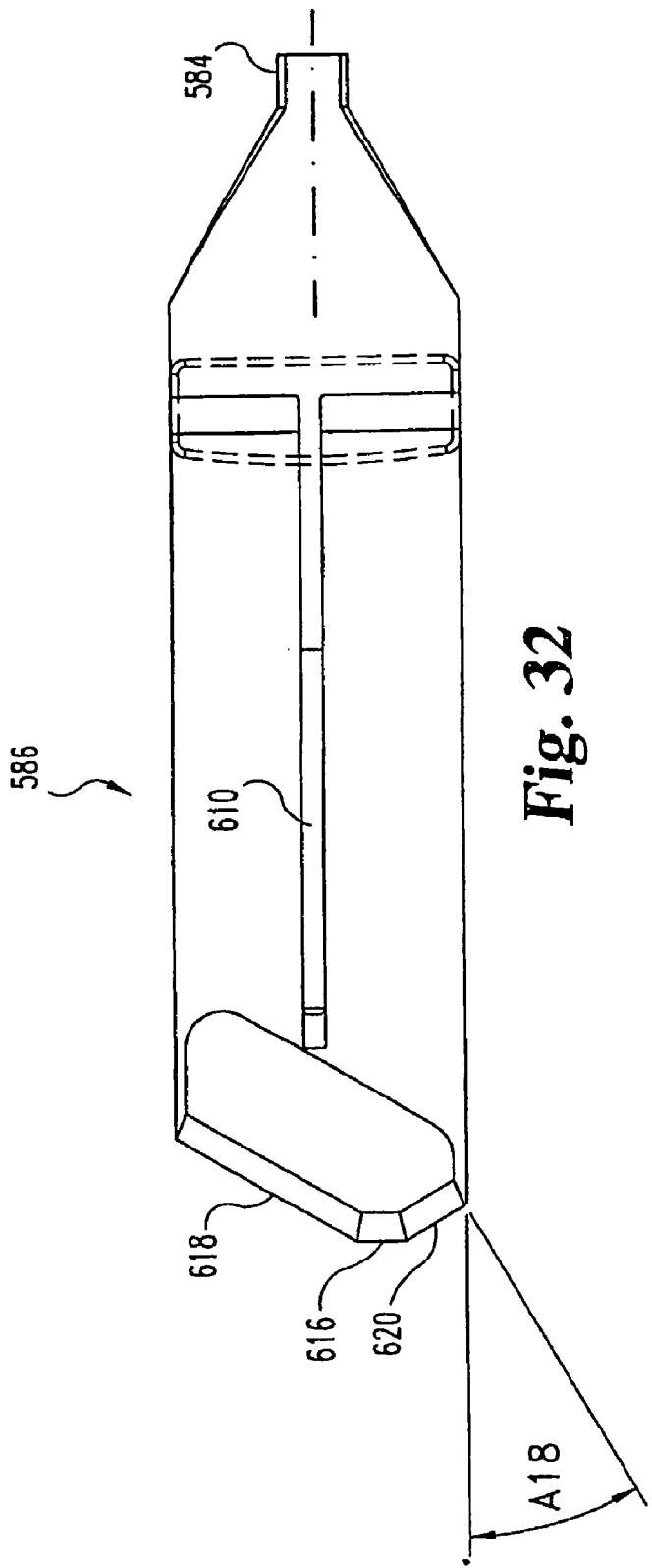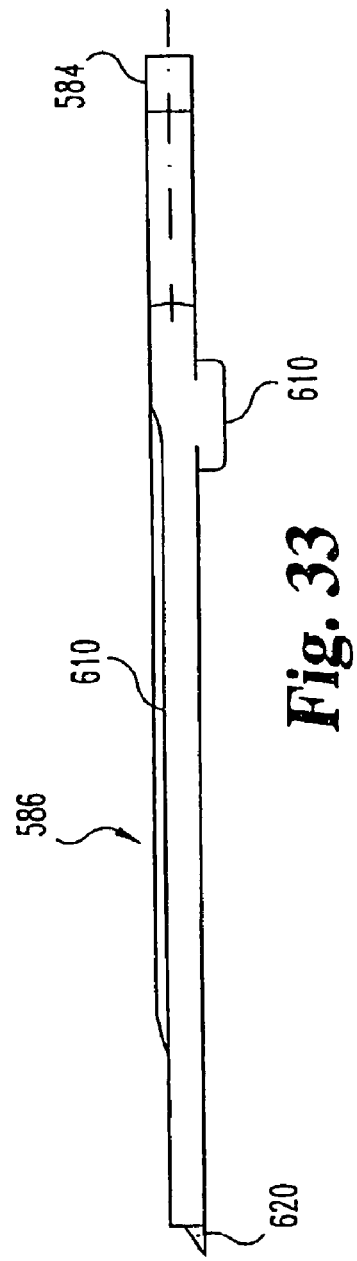

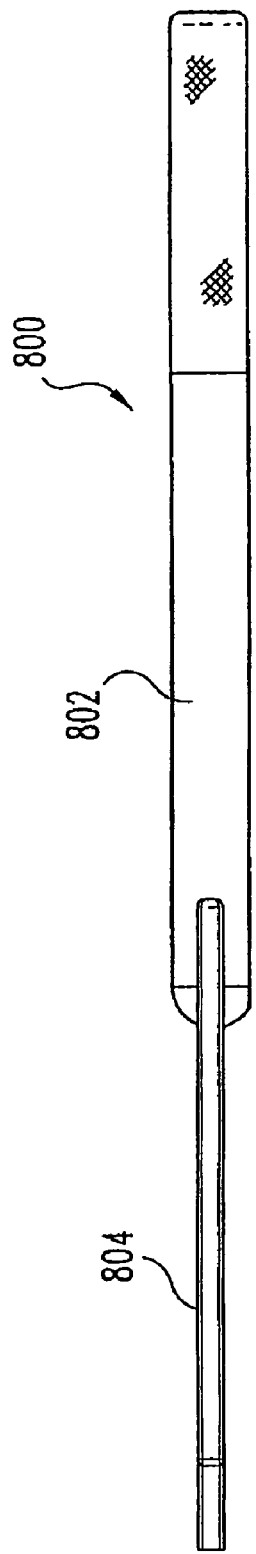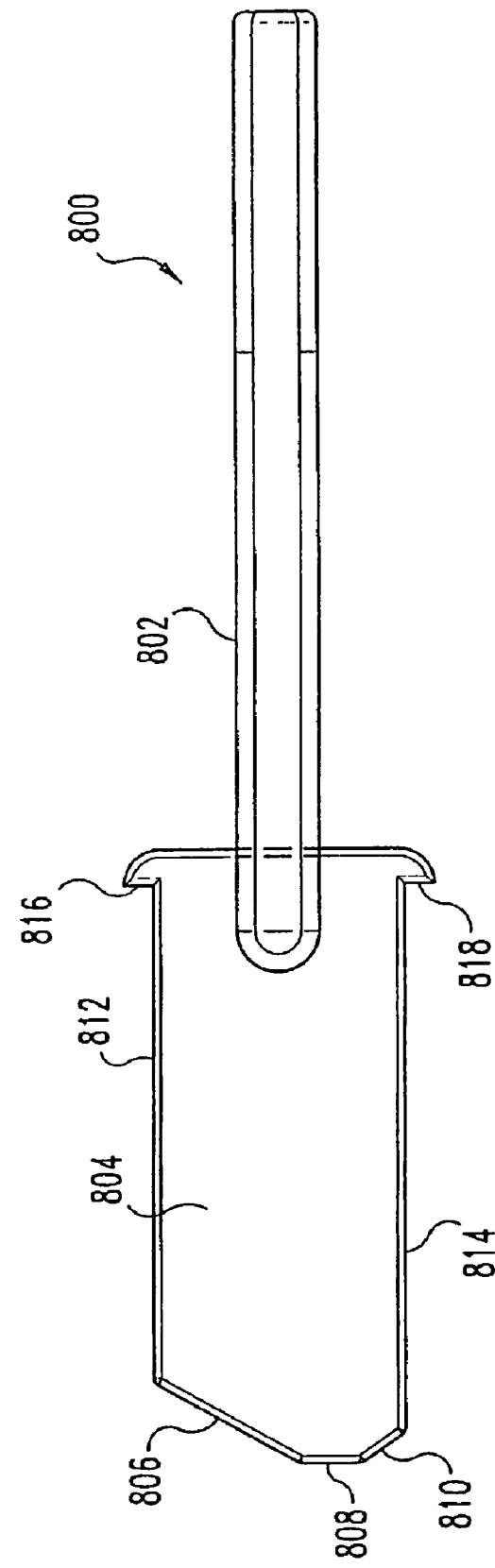

INSTRUMENTS AND TECHNIQUES FOR DISC SPACE PREPARATION

CROSS-REFERENCE TO RELATED APPLICATIONS

The present application is a divisional of U.S. patent application Ser. No. 10/219,040 filed on Aug. 14, 2002 now U.S. Pat. No. 7,033,362, which is a continuation of PCT Patent Application Serial No. PCT/US01/05500, filed Feb. 22, 2001 entitled "Instruments and Techniques for Disc Space Preparation" which was published in English under Article 21(2) and which claims the benefit of U.S. Provisional Patent Application Ser. No. 60/184,107 filed Feb. 22, 2000 entitled "Instruments and Techniques for Disc Space Preparation", all of which are hereby incorporated by reference in their entirety.

BACKGROUND OF THE INVENTION

The present invention relates generally to instruments and techniques for preparing a site between two adjacent bony segments to receive an implant therebetween. More specifically, the present invention provides instruments for vertebral end plate preparation to receive interbody fusion devices or artificial disc implants. The instruments and techniques of the present invention have particular application, but are not limited to, direct anterior or oblique-anterior approaches to the spine.

While implants of various types have been utilized throughout the body for various orthopedic bone applications, the present invention has particular application to the field of preparing an intervertebral disc space to receive an interbody fusion device to create bony fusion or a spacer providing artificial disc functions. Such procedures may be necessary where the natural disc has degenerated or slipped resulting in pain and discomfort to a patient. The deterioration or movement of the disc often results in the two adjacent vertebral bodies coming closer together. A common treatment is to surgically restore the proper disc space height to thereby alleviate the neurologic impact of the collapsed disc space. Typically, the damaged disc is removed and an alternative substance is inserted to maintain the proper height. While artificial discs have been developed and will likely continue to be developed that may be placed in the effected disc space, present procedures often utilize a load bearing structure, either man-made or natural, to maintain the disc height and promote bony fusion between the adjacent vertebrae. Such techniques for achieving interbody fusion between adjacent vertebral bodies is well-known in the art, it will not be described further.

U.S. Pat. No. 5,772,661 to Michelson discloses methods and instrumentation for surgical correction of human thoracic and lumbar spinal disease from an anterior, lateral aspect of the spine. This patent discloses methods, techniques, and instruments for lateral placement of spinal implants. While the application does recognize that an approach from a lateral aspect of the spine in an area of lordosis may result in angulation between the end plates adjacent vertebra, this invention teaches only restoration of the proper angle between the vertebra. Subsequent preparation of the opening to receive an implant, however, is created by over cutting into the end plates of the adjacent vertebra disposed closest and potentially under preparing the end plates disposed farther apart. Thus, there is a need for end plate preparation which not only maintains lordotic angulation of adjacent vertebra, but also provides for substantial uniform preparation of the vertebral end plates to receive an implant.

International publication WO 98/04202 published Feb. 5, 1998 discloses milling instrumentation and methods for preparing a space between adjacent vertebral bodies. This publication discloses utilization of a milling device to control the depth of penetration and field of cut of cutting instruments adapted to prepare vertebral end plates to receive an implant. However, as with earlier approaches to end plate preparation, this publication fails to teach instruments utilized to provide precise control over cutting depth, height, and angulation. Such drawbacks are particularly acute when it is considered that an oblique approach to the anterior spine may be necessary where patient anatomy does not permit easy direct anterior access to the spine.

Thus, there remains a need for improved instrumentation and techniques for disc space preparation. The present application is directed to those needs.

SUMMARY OF THE INVENTION

The present invention provides a variety of instruments for precision guided disc space preparation. While various approaches to the spine may make use of the instruments according to the present invention, the instruments are preferably adapted to a direct-anterior or oblique-anterior approaches to the spine. Additionally, the present invention contemplates novel methods for disc space preparation utilizing the guided instrumentation of the present invention.

One aspect of the invention includes a distraction window assembly provided with removable distraction flanges adapted to be removably received within the window assembly. In a preferred embodiment, a retaining clip is provided that releasably locks the flanges in position during use. In a further preferred aspect, the distraction window includes arcuate upper and lower bone engaging surfaces to provide intimate contact with the vertebral bodies.

In yet another aspect of the invention, a guide tube is provided for guiding instruments and implants there through. The guide tube acts to align the instruments and implants as well as protect surrounding tissue from damage during the various steps of a procedure. The guide tube includes an external locking mechanism operable to lock the guide tube to the window assembly from the proximal end of the guide tube. Preferably, the locking mechanism is operable without rotation of the guide tube. The external locking mechanism permits an unobstructed internal working channel and is operable without addition vessel retraction.

In still a further aspect of the present invention, a burr template is provided for mating engagement with the window assembly. The burr template may preferably include a guide housing having a cutting slot, a linkage assembly connected to the housing and a guide tube connected to the linkage. The guide tube is controlled to move laterally along the cutting slot while maintaining alignment of the cutting piece in the horizontal and vertical directions. Still more preferably, the guide tube is maintained at an oblique angle with respect to the housing. Additionally, the burr template may provide the capability of controlling the height of the burr cut into the vertebral body end plate. The burr template assembly includes an incremental adjustment mechanism adapted to provide defined incremental adjustments of the height or depth of burr cutting into the end plate for precision milling of the end plates. In a preferred aspect, the burr template end face may be angled with respect to the distraction window such that a burr may be controlled to remove an angled surface of the end plate.

The present invention also includes a guide assembly for a bladed cutting instrument. The guiding assembly includes a slot adapted to receive a blade and a guide channel for maintaining alignment of the blade in the slot. In a preferred aspect, the slot and guide channel are disposed at an oblique angle permitting removal of a portion of a vertebra. In still a further preferred aspect, the guiding assembly is adapted for guiding instruments into the spine from an oblique-anterior approach. In this further aspect, the guiding assembly includes angulation to account for the oblique angle approach to the spine and compounding angulation to create the desired angle of the removed vertebral bone.

The present invention further contemplates a distractor for an oblique-anterior approach to the spine. In one preferred aspect, the distractor includes a substantially straight leading portion and an angled leading portion. Still further, it is preferable for maintaining or establishing angulation between adjacent vertebrae that the distractor have a head with a tapered portion oriented at an angle with respect to the longitudinal axis of the distractor. In one preferred embodiment, the offset is approximately 30 degrees.

The invention further contemplates a distraction window configured for oblique engagement to the spine. In one preferred aspect, the bone engaging surfaces are arcuate and including a leading portion extending more distally than a trailing portion. In still a more preferred embodiment, the distraction window includes distraction flanges configured to maintain angulation between adjacent vertebrae. The flanges preferably include a taper oriented at an offset with respect to the longitudinal axis.

In still a further aspect of the invention, a chisel adapted for oblique cutting of the vertebra is provided. The chisel comprises a first straight cutting edge and a second angled cutting edge. In a preferred aspect, the chisel further includes a third angled cutting edge shorter than the first angle portion.

The present invention further contemplates a method of disc space and endplate preparation from an anterior approach to the spine as further described and disclosed herein. Still more preferably, the anterior approach is from an oblique angle to the spine. In this aspect, the method includes gaining access to an oblique portion of the spine, inserting a distractor from an oblique angle and engaging a distraction window from the oblique angle. A cutting guide may then be engaged with the distraction window and the endplates may then be prepared from the oblique angle. In a preferred aspect, the endplates are prepared to include a taper between adjacent vertebrae.

These and other objects of the present invention will become apparent from a review of the accompanying drawings and the detailed description of the drawings.

BRIEF DESCRIPTION OF THE DRAWINGS

FIG. 3 is a perspective view of the drawing of FIG. 1 further including a guiding assembly according to another aspect of the present invention.

FIG. 5a is a perspective view of a distraction window according to one aspect of the present invention.

FIG. 5b is a top view of the distraction window of FIG. 5a.

FIG. 5c is a side view of the distraction window of FIG. 5a.

FIG. 6a is an exploded perspective view of an alternative embodiment of a distraction window according to another aspect of the present invention.

FIG. 6b is a side view of the distraction window of FIG. 6a.

FIG. 6c is a front view of the distraction window of FIG. 6a.

FIG. 6d is a top view of the distraction window of FIG. 6a.

FIG. 7a is a side view of a retaining shaft for use with the guide sleeve of the present invention.

FIG. 7b is an end view of the guide shaft of FIG. 7a.

FIG. 11a is a side view of the rotary cutting guide of FIG. 9.

FIG. 11b is a rear view of the rotary cutting guide of FIG. 1a.

FIG. 11c is a front view of the rotary cutting guide of FIG. 11a.

FIG. 11d is a bottom view of the rotary cutting guide of FIG. 11a.

FIG. 11e is a top view of the rotary cutting guide of FIG. 11a.

FIG. 12a is a partial cross-sectional top view of a guide tube according to another aspect of the present invention.

FIG. 12b is an end view of the guide tube of FIG. 12a.

FIG. 13a is a perspective view of a guide tube linkage according to the present invention.

FIG. 13b is an end view of the guide tube linkage of FIG. 13a.

FIG. 13c is a side view of the guide tube linkage of FIG. 13a.

FIG. 15b is a side view of the guide block of FIG. 15a.

FIG. 15c is a rear view of the guide block of FIG. 15a.

FIG. 15d is a front view of the guide block of FIG. 15a.

FIG. 15e is a cross-sectional side view taken along line 15e-15e of FIG. 15d.

FIG. 16 is a perspective view of a cutting blade guide assembly according to another aspect of the present invention.

FIG. 18b is a side view of the chisel blade of FIG. 18a.

FIG. 19b is an enlarged perspective view of the implant insertion assembly according to FIG. 19a.

FIG. 20b is a perspective view of the implant and vertebral body of FIG. 20a.

FIGS. 22a through 22c are bottom, side and top views, respectively, of the distractor of FIG. 21.

FIGS. 23a through 23d are top, rear end, front end and partial cross-section side view, respectively, of the distractor head of FIG. 21.

FIG. 23e is perspective side view taken along line 23e-23e of FIG. 23a.

FIG. 29 is a perspective view of a guide block assembly and chisel.

FIG. 30a is a side view the guide block of FIG. 28.

FIG. 30b is a front end view of the guide block of FIG. 30a.

FIG. 30c is a rear end view taken along line 30c-30c of FIG. 30a.

FIG. 31b is a front end view of the guide block of FIG. 31a.

FIG. 31c is a rear end view taken along line 31c-31c of FIG. 31a.

FIG. 32 is a top view of a chisel blade according to the present invention.

FIG. 33 is a side view of the chisel blade of FIG. 32

FIGS. 41a and 41b are a top view and side view, respectively, of the depth gauge of FIG. 40.

DESCRIPTION OF THE PREFERRED EMBODIMENTS

Figure 1:
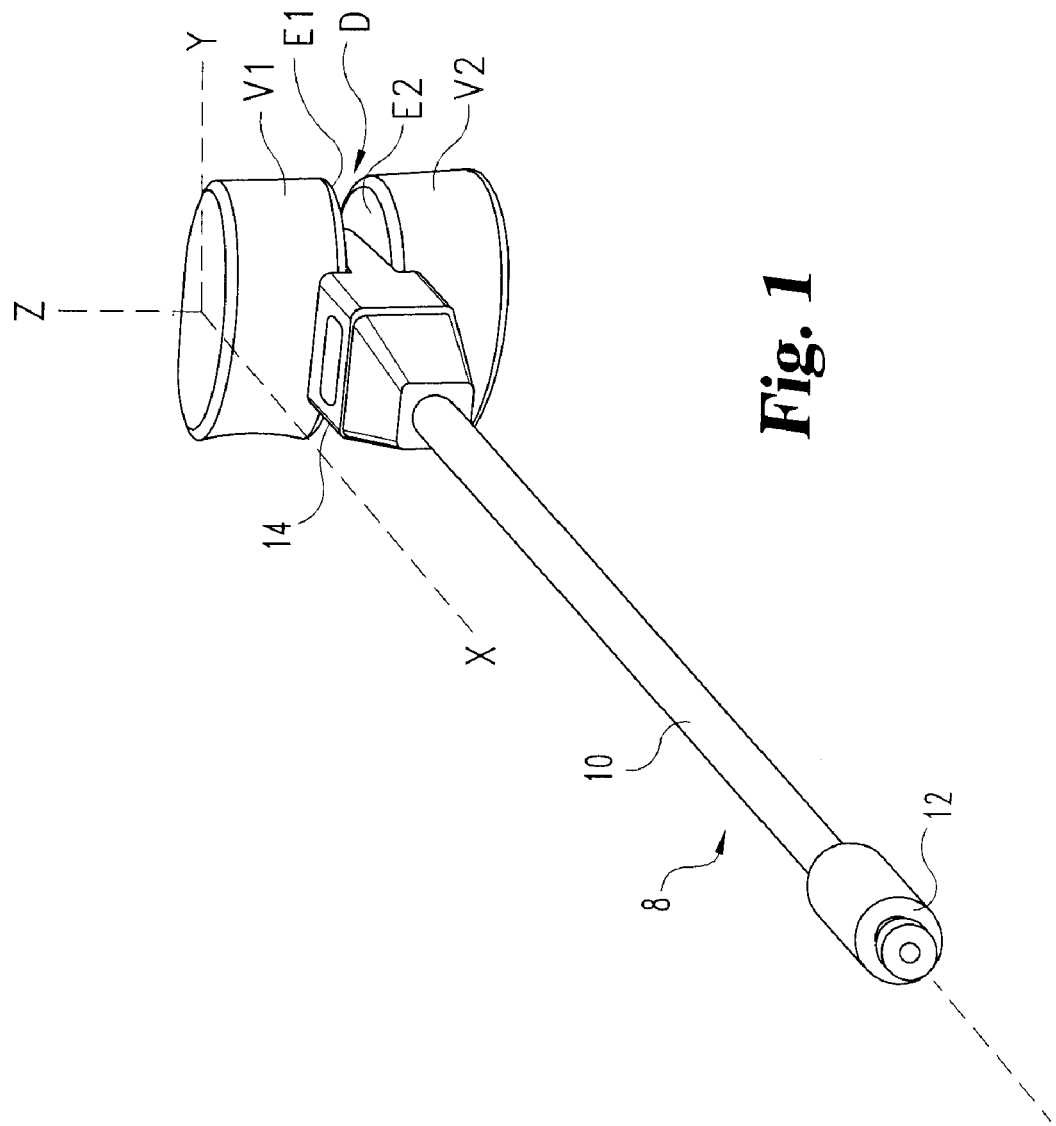
FIG. 1 is a perspective view of a distractor disposed between two adjacent vertebral bodies from a direct anterior approach to the spine.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

The present invention relates to instruments and methods for gaining access to a disc space between adjacent vertebral bodies, distracting the disc space to a desired height, preparing the disc space to receive an implant to maintain disc space height and angulation, and a method for inserting an implant into the prepared disc space. More specifically, while methods and instruments disclosed in the present application may have application in other areas of the spine or the body, it is specifically contemplated that the present instruments and method may be utilized in an anterior approach to the spine for implantation of various implant devices. Still more specifically, the present invention contemplates a direct anterior approach to the spine for implant placement as well as an anterior-oblique approach to the spine for disc space preparation and implant placement. It will be understood that an anterior-oblique approach to the spine may be desirable in certain areas of the spine where a direct anterior approach is difficult or impossible because of patient anatomy. The term implants in the present application is used in a broader sense to encompass both load bearing implants constructed of man-made materials, as well as load bearing implants formed of naturally occurring materials. Further, implants contemplated to be used with the present invention may include those intended to promote fusion between adjacent vertebra as well as artificial disc replacements. Implant inserters and specific implants are disclosed in U.S. Provisional Application entitled "INSTRUMENTS AND IMPLANTS FOR MULTI-DIRECTIONAL INSERTION OF A VERTEBRAL SPACER," filed Feb. 22, 2000, which is incorporated herein by reference in its entirety.

Referring now to FIG. 1, there is shown a partial spinal column consisting of vertebra V1 and vertebra V2 separated by a disc space D. It will be understood that access to disc space D is obtained by known surgical techniques and will not be described further herein. With the disc space D exposed, distractor 8 is positioned adjacent disc space D from a direct anterior approach. With respect to the view of FIG. 1, the X axis represents the anterior to posterior direction, the Y axis extends laterally, while the Z axis extends in the superior to inferior direction. As shown in FIG. 1, distractor 8 is inserted substantially parallel to the X axis. The position of distractor 8 in terms of anatomical position is substantially parallel to the sagittal and axial planes. Distractor 8 includes an elongated shaft 10 having a proximal end with a tool adapter 12 to receive a tool handle (not shown) and a distal end having a distraction head 14.

Figure 2A:
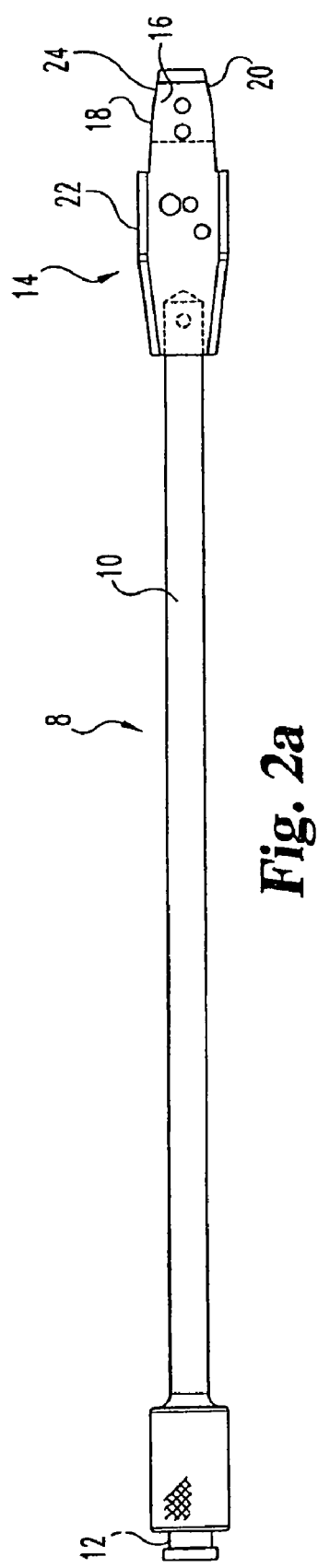
FIGS. 2a and 2b are a side and top view, respectively, of the distractor of FIG. 1.
Figure 2B:
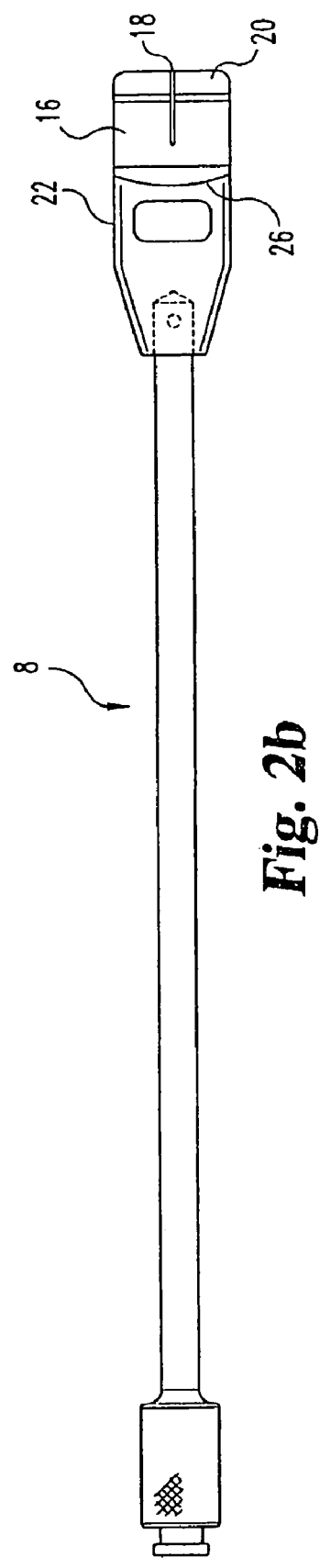

Referring to FIGS. 2a and 2b, distraction head 14 further comprises opposing tapered leading surfaces 20 and 24 adapted to engage and spread the vertebrae as the surfaces are advanced into the disc space D. A guiding fin 18 is centrally disposed on distraction head 14. Guiding fin 18 has a height greater than tapered leading surfaces 20 and 24 as well as the overall height of distraction plug 16 such that guiding fin 18 may extend into the vertebral bone and guide the distractor into the desired position. The use of a guiding fin on a distractor is further disclosed in U.S. patent application Ser. No. 09/418,741, which is incorporated herein in its entirety. Distraction plug 16 may take many known configurations including having tapered surfaces adapted to establish and maintain desired angulation between adjacent vertebrae. Further, distractor head 14 includes an arcuate bone engaging surface 26 and an opposing bone engaging surface on the bottom side, each adapted to engage the anterior portions of the respective upper and lower vertebral bodies.

In use, distractor 8 of FIG. 1 is disposed adjacent disc space D. Force is applied to shaft 10 to urge distractor head 14 into disc space D. As distractor head 14 advances into disc space D tapered leading surfaces 20 and 24 engage end plates E1 and E2, respectively urging vertebra V1 and V2 apart and maintaining the distraction height by disposing the rest of distraction plug 16 within disc space D.

Referring now to FIGS. 3 through 5d, there is shown a guide tube assembly adapted to be received over distractor 8 of FIG. 1. Guide tube assembly includes a distraction window 30 and a selectively coupled guide tube 32 with a removable guide cap 34. Referring more specifically to FIGS. 5a-5d, distraction window 30 includes a working channel 45 configured to slidingly receive centering block 22 of distractor 8. Extending distally from distraction window 30 is distraction holder 36 and opposing distraction holder 40. The distraction holders are adapted and configured to extend into the disc space D and engage end plates E1 and E2 to maintain the distraction obtained with distractor 8. Further, each of the distraction holders includes an external taper on its leading surface adapted to urge tissue to the exterior of the window and away from working channel 45. Distraction holders also include bone engaging surfaces, such as ridges 47 and 49 shown in FIG. 5c with respect to distraction holder 40, to inhibit dislodgment once positioned in the disc space. Additionally, distraction window includes arcuate bone engaging surfaces 42 and 44 adapted to engage the arcuate anterior portions of V1 and V2, respectively. Preferably, a spike 38 extends from bone engaging surface 42. Spike 38 is intended to penetrate vertebra V1 to provide additional stability to distraction window 30. Working channel 45 is interrupted by annular shoulder 46 marking the transition from the proximal portion 51 of larger dimension to the smaller dimensions of the distal working area 53 of distraction window 30. The distal working area 53 includes slightly tapering side walls. Distraction window 30 also includes a recess 48 on its upper surface.

Figure 4:
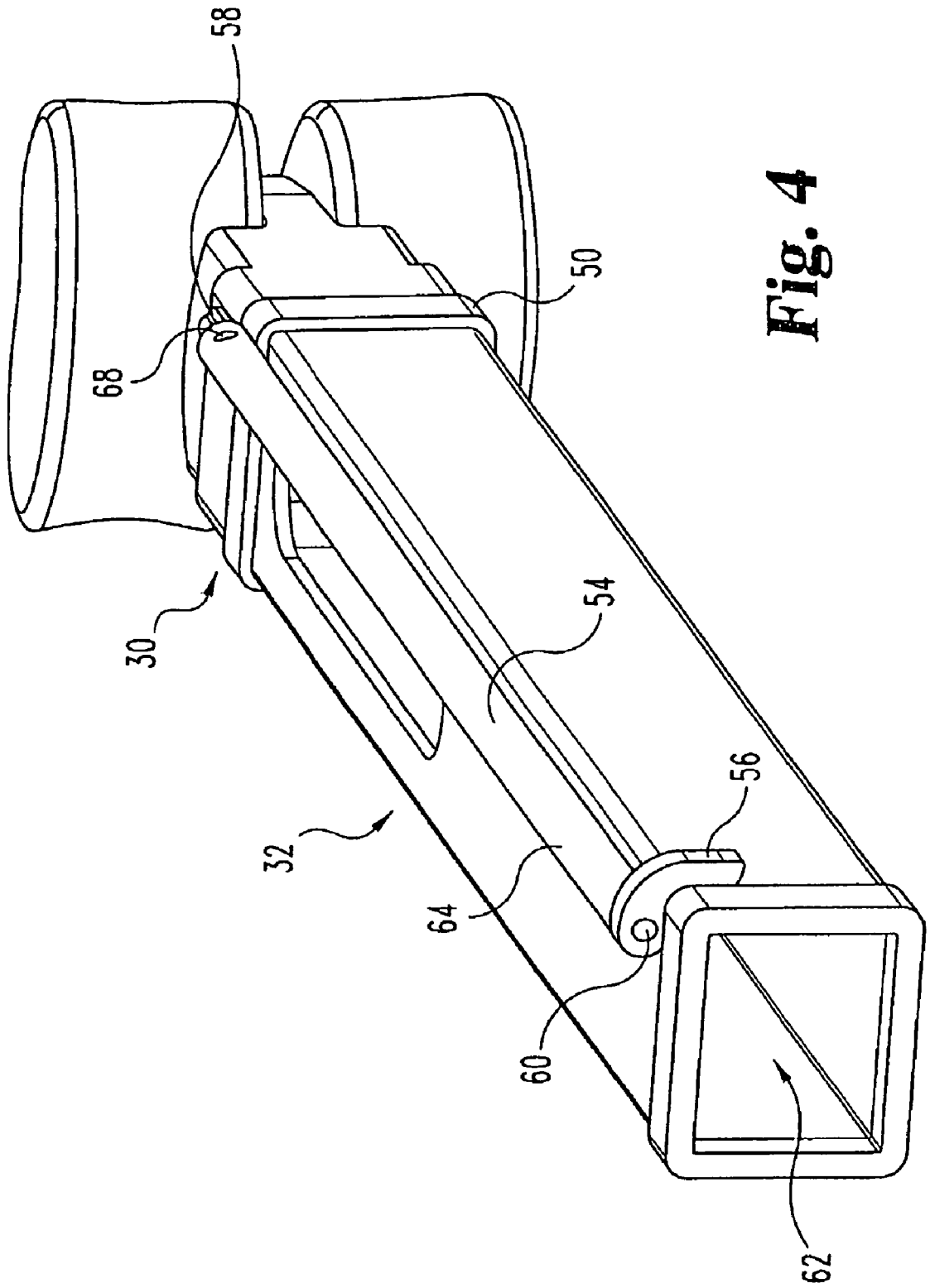
FIG. 4 is a perspective view of the guide assembly of FIG. 3 positioned adjacent the disc space and the distractor removed.
Figure 5D:
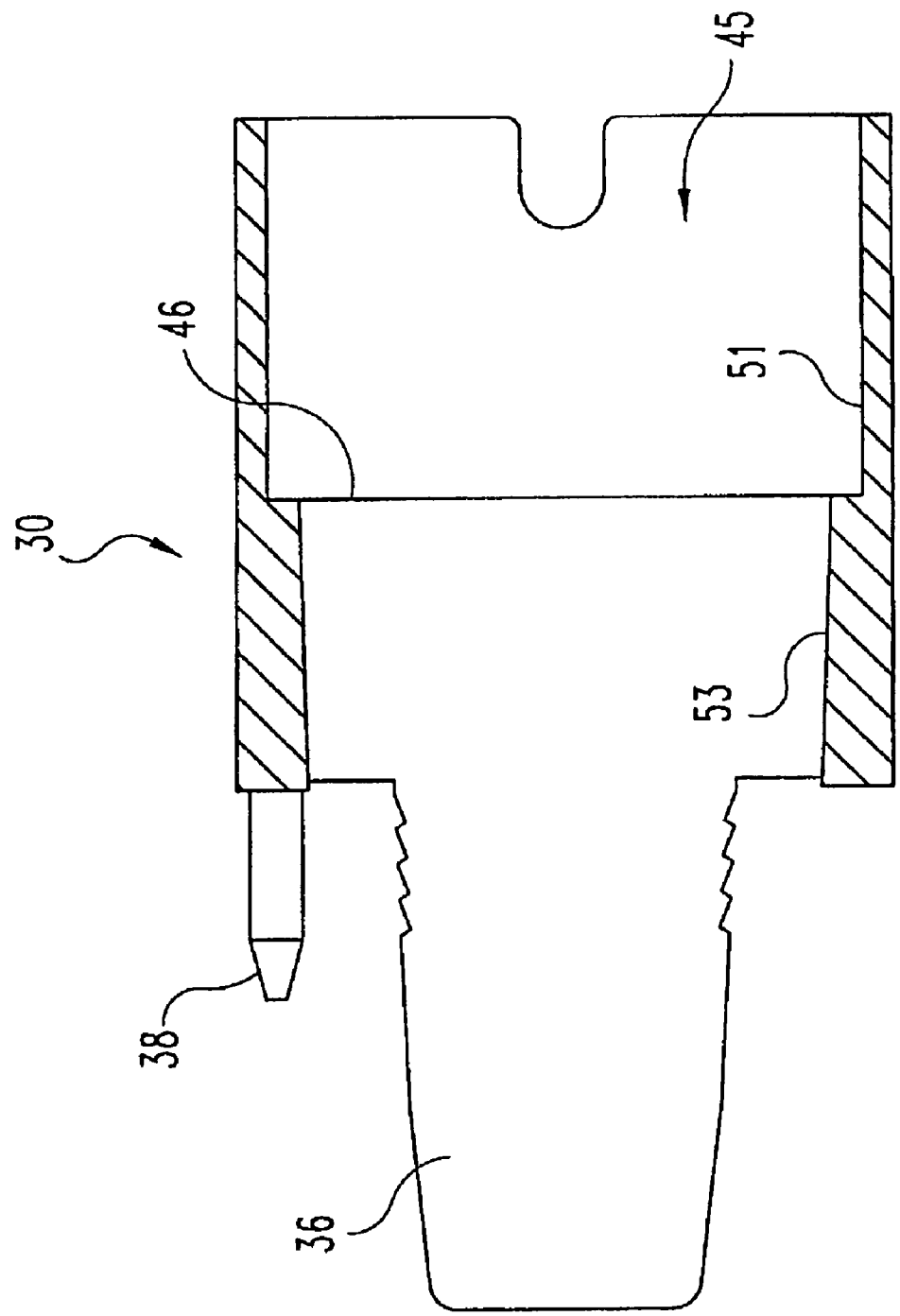
FIG. 5d is a cross-sectional side view taken along line 5d-5d of FIG. 5b.

Guide tube 32 includes a substantially rectangular working channel 62 adapted and configured to correspond with the proximal dimensions of working channel 45 of distraction window 30. While a rectangular working channel is disclosed in the present application, it will be understood that it is contemplated that working channels having substantially circular, oval, FIG. 8 or any other cross-sectional configurations may be utilized for disc space preparation and implant insertion. Guide tube 32 includes a front flange adapted to engage the proximal portion of distraction window 30. Guide tube 32 also includes retaining assembly 54 that may be utilized to selectively couple guide tube 32 to distraction window 30. Referring to FIG. 4, retaining assembly 54 includes an outer shaft 64 coupled to guide tube 32. An inner shaft 60 extending along the length of outer tube 64. A finger lever 56 coupled to the proximal end of inner shaft 60 and a retaining foot 58 disposed on the distal portion of inner shaft 60. Inner shaft 60 is shown in more detail in FIGS. 7a and 7b. The position of inner shaft 60 with respect to outer shaft 64 is maintained by pin 68 extending into annular groove 70.

An alternative version of a distraction window assembly is shown in FIGS. 6a-6d. Distraction window assembly 80 includes selectively coupled distraction holders 82 and 84. It will be understood that distraction holders of various heights and angulations may be utilized with distraction window body 81 thereby providing a reduced number of window assemblies that must maintained in a sterilized condition for use by the operating staff. Distraction holders 82 and 84 may be quickly inserted or changed to meet the various demands of a particular surgery simply by removing retaining clip 86.

Distraction holder 82 includes a pair of opposing dove tail projections 98 and 100. A corresponding channel 92 is formed in distraction window body 81. Channel 92 includes a pair of opposed dove tail recesses 94 and 96 adapted to matingly receive dove tail projections 98 and 100, respectively. Retaining groove 104 extends on the upper portion of distraction window body 81 as well as along the sides of the distraction window assembly. Retaining groove 104 extends into channel 92 and in a similar fashion with respect to the retention of distraction holder 84. The intersection of channel 92 and 93 with retaining groove 104 creates openings 102 and 106, respectively. Groove 83 is formed on distraction holder 82 such that when disposed within channel 92 groove 83 is substantially aligned with slot 102. Distraction holder 84 is configured in substantially similar manner to mate with channel 93 and includes a similar retaining groove to align with slot 106. With distraction holder 82 disposed within channel 92 with the proximal portion abuttingly received against end wall 108, retaining ring 86 may be positioned within groove 104 thereby extending a portion of retaining ring 86 into groove 83 to hold distraction holder within the distraction window body 81.

Distraction window body 81 further includes an upper and lower projection 90 and 88, respectively. Projections 90 and 88 further include bores 91 and 89, respectively, configured to receive pins that may extend into the vertebra to further retain the distraction window assembly in relation to the vertebral bodies. Further, pins extending through bores 91 and 89 tend to maintain arcuate vertebral bone engaging surfaces 114 and 116 in intimate contact with the anterior portions of the vertebral bodies. Thus, distraction window assembly 80 defines a working channel 112 for access to the disc space and portions of the upper and lower vertebral bodies.

Figure 8:
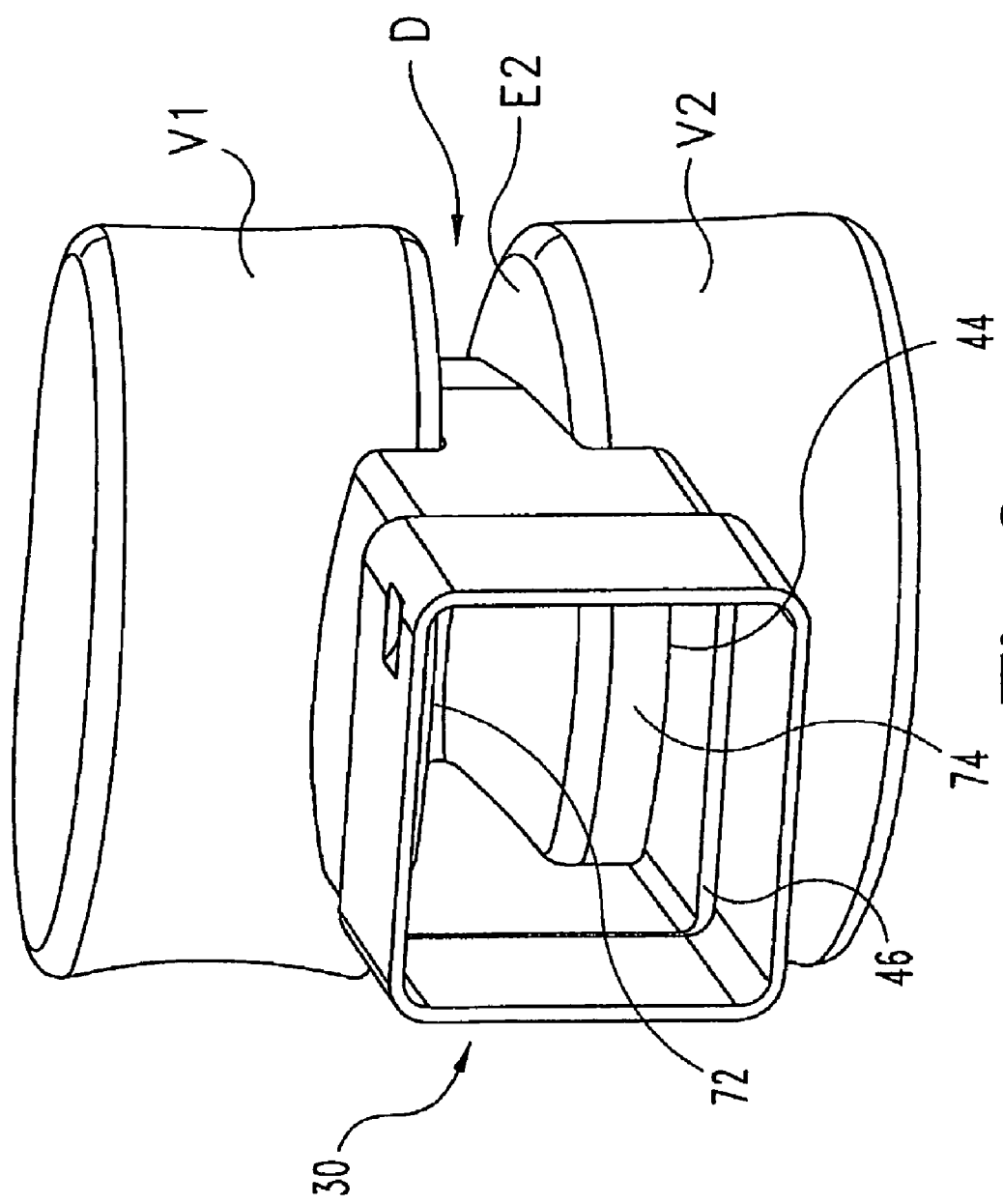
FIG. 8 is a perspective view of a distraction window according to the present invention disposed between adjacent vertebrae.

Distraction window 30 may be coupled to guide tube 32 by initially bringing guide tube 32 into a butting engagement with distraction window 30 such that flange 50 surrounds at least a portion of distraction window 30. Lever 56 may then be rotated to cause retaining foot 58 to rotate into recess 48 on distraction window 30. With retaining foot 68 extending into recess 48, distraction window 30 and guide tube 32 are thereby removably coupled to one another. Referring now to FIG. 3, the guide tube and distraction window assembly may then be advanced over distractor 8 with the distraction window assembly 30 guided into place by engagement with centering block 22 of distractor 8. Cap 34 may be positioned over flange 52 and force applied to the cap, such as by hammering, to advance distraction holders 36 and 40 into the disc space and pin 38 into the bone of the vertebra. Once the guide tube and distraction window assembly have been properly positioned, cap 34 may be removed and a handle attached to distractor 8 at coupling 12. Once a handle is attached to coupling 12, distractor 8 may then be forcibly removed from the disc space leaving the guide tube and window assembly positioned as shown in FIG. 4. Lever 56 of retaining assembly 54 may then be rotated in an upward direction thereby causing retaining foot 58 to rotate out of recess 48 on distraction window 30. With retaining foot 58 positioned out of recess 48, guide tube 32 may be disengaged from distraction window 30. Thus, as shown in FIG. 8, distraction window 30 retains it's position in the disc space and adjacent the anterior portions of vertebra V1 and V2 with distractor holders 36 and 42 engaging end plates E1 and E2 to maintain the disc space height and angulation established by distractor 8. As shown in FIG. 8, portion 72 of vertebra V1 and portion 74 of vertebra V2 are accessible through distraction window 30.

Referring now to FIGS. 9-15e, there is shown a rotating tool guide adapted for utilization with a distraction window 30 according to the present invention. Guide assembly 120 includes a guide housing 125 shown in greater detail in FIGS. 15a-15e. Guide housing 125 includes an insert end 124 configured to be received within proximal portion 51 of distraction window 30. It will be understood that distal end 127 of guide housing 125 abuttingly engages wall 46 in distraction window 30. Further, the walls of insertion end 124 are configured to be a substantially close fit with the walls defining proximal portion 51 of distraction window 30. Further, surface 123 of guide housing 125 is configured to engage the proximal most portion of distraction window 30. Thus, guide housing 125 is adapted to have insertion portion 124 matingly received within the proximal portion 51 of window assembly 30. Insertion end 124 is a substantially close fit with the dimensions of proximal portion 51 such that there is little movement of the guide housing with respect to the distraction window in directions other than proximally toward the user.

Guide housing 125 further includes cutting window 128. In a preferred embodiment, particularly useful for fashioning vertebral end plates to establish and/or maintain angulation between adjacent vertebra, upper surface 176 and lower surface 177 of cutting window 128 are disposed at an angle A1 with respect to the longitudinal axis 179. Flange 129 is disposed within cutting window 128 and may act as a bearing surface for elements of the guiding assembly. As further described herein, the angulation of cutting window 128 with respect to the longitudinal axis 179 permits end plate cutting and preparation at an angle desirable to maintain and/or establish an angular relationship between adjacent vertebrae. Further, guide face 126 and flange 129 are set at a corresponding angle A2 with respect to the longitudinal axis. It will be understood that the angulation of guide face 126 provides a side wall 142 that tapers between the upper surface 144 to a greater thickness at bottom surface 146. Thus, guide face 126 and flange 129 provide a reference plane for the attachment of other guiding elements such that they may be maintained in the proper angular relationship with the angle of cutting window 128. Internally threaded bore 178 is defined in housing 125 and is disposed at an angle substantially equal to a angle A1. In a preferred embodiment, threaded bore 174 is disposed equidistant between sidewalls 142 and 143 such that it is substantially centered with respect to the lateral dimensions of guide block 125.

Guide assembly 120 further includes a guide tube 130 shown in greater detail in FIGS. 12a and 12b. Guide tube 130 includes a through channel 131 having a proximal end with an internal chamfer 152 configured to guide and align a tool shaft as it is inserted. Further, internal channel 131 includes an annular flange 154 dividing areas of larger and small diameter of working channel 131. In a preferred embodiment, guide tube 130 is interconnected by linkage 132 to a linkage post 156. Preferably, the interconnection between guide tube 130, linkage 132, and guide post 156 is substantially rigid and does not permit pivotal movement of one member with respect to the other. Guide post 156 further includes an axial bore 158 defining an internal thread. Another component of guide assembly 120 includes guide post 134 having an axial bore 164 extending there through. Preferably, guide post 134 is rigidly interconnected with linkage tube 160. Linkage tube 160 includes an axial bore 162 extending there through.

Guide assembly 120 is assembled by placing linkage post 156 within bore 162 of linkage tube 160. Assembly screw 150 is then inserted with external threads threadedly engaging the internally threaded bore 158. Head 170 is sized to be larger than bore 162 such that assembly screw 150 retains linkage. Assembly screw 150 may be tightened by a tool-engaging slot if desired. The interconnection between linkage post 156 and linkage tube 160 permits rotation of linkage tube about linkage post. Distal portion 133 of guide tube 130 is then disposed within window 128 and guide post 134 is aligned with threaded opening 174 such that internal bore 164 is in substantial alignment with threaded bore 174. An elongated assembly screw with a shaft sufficient to extend through bore 164 is utilized to attach guide post 134 to housing 125. The connection between housing 125 and guide post 134 permits pivoting of guide post 134 about the shaft of assembly screw 148. Further, as shown in FIG. 11a, guide tube 130 and guide post 134 are disposed at an angle A1 with respect to the longitudinal axis 179 of housing 125. Thus, guide tube is in substantial alignment with cutting window 128 and will be maintained in substantial alignment throughout the cutting process.

Figure 14:
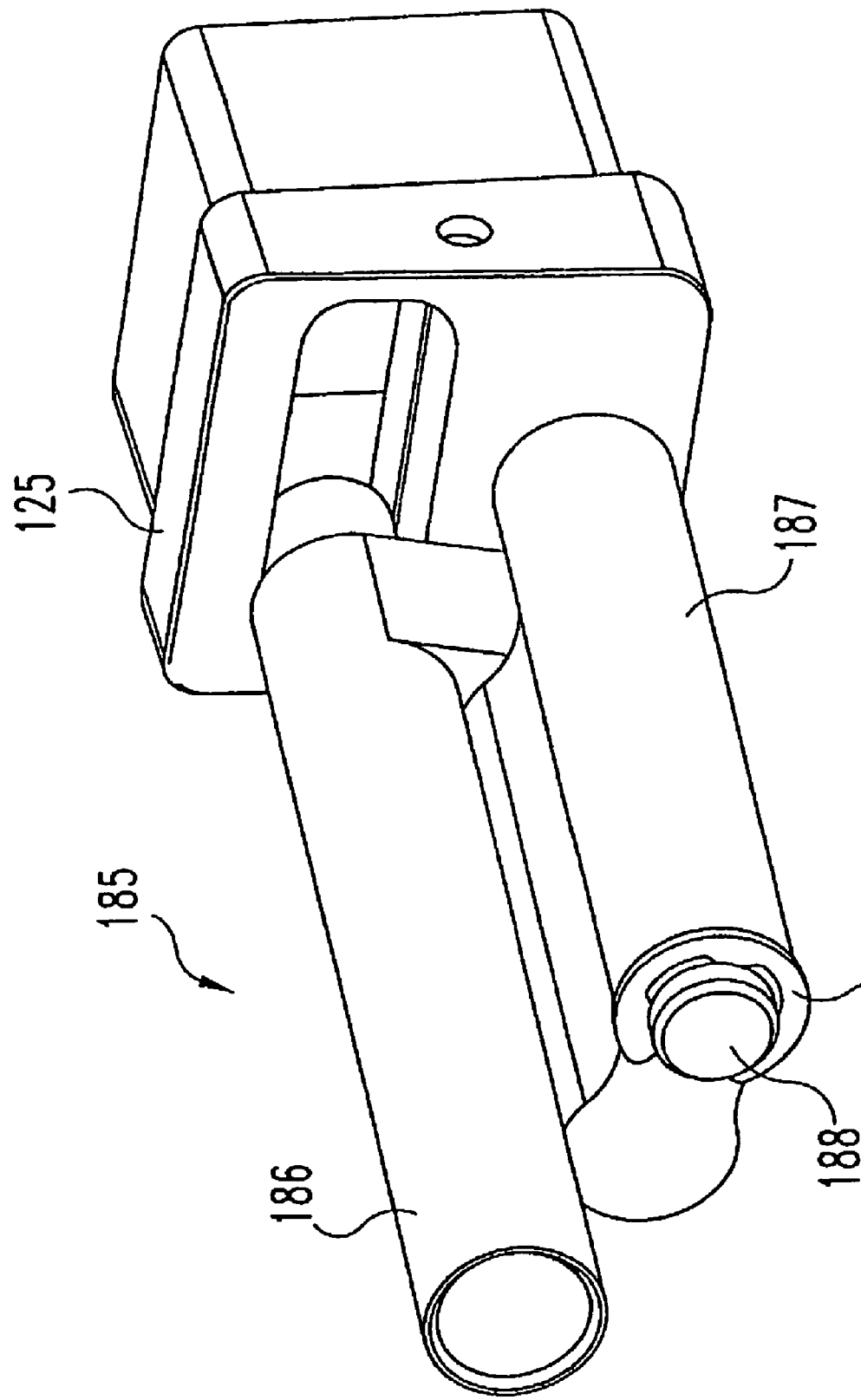
FIG. 14 is a perspective view of an alternative guide tube assembly according to the present invention.
Figure 15C:
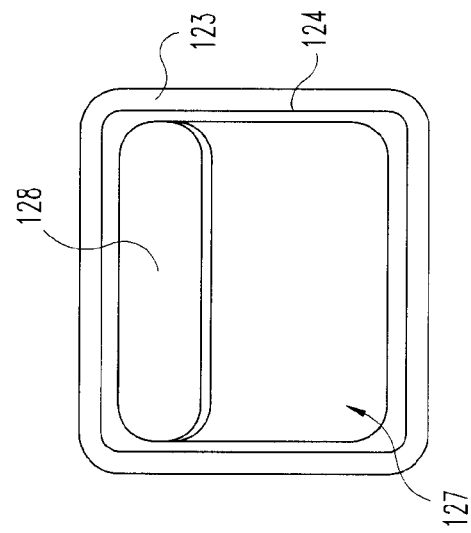
Figure 15A:
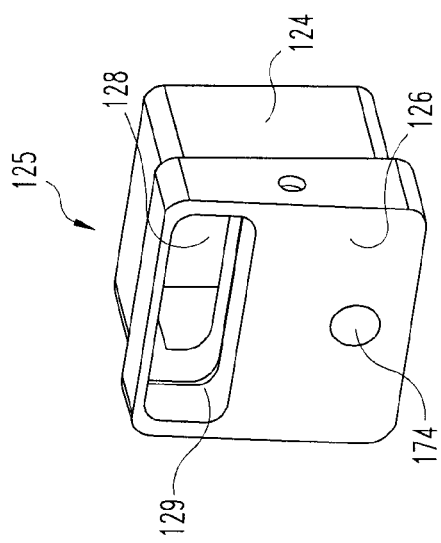
FIG. 15a is a perspective view of a guide block according to the present invention.
Figure 15B:
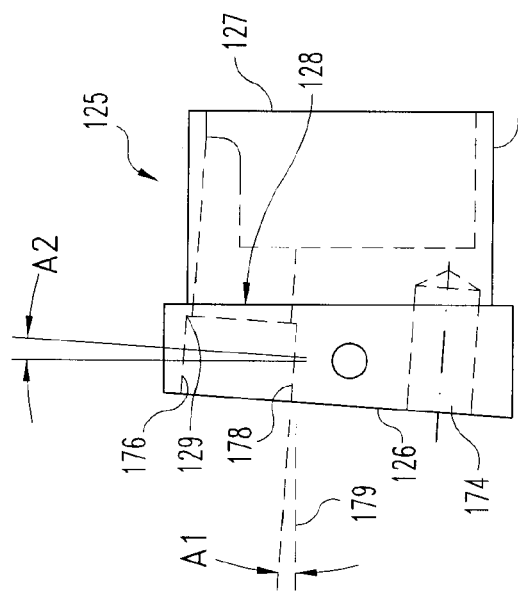

Referring to FIG. 14, an alternative embodiment of a guiding assembly according to the present invention is shown. Guiding assembly 185 includes a housing 125, guide tube 186 and linkage 187. A portion of guide tube 186 is received within linkage 187 as described above with respect to the embodiment of FIG. 9. Post 188 extends the length of linkage 187 and fixedly engages housing 125. Post 188 may be engaged to housing 125 by, but without limitation, threads, pinning, welding, adhesive, or any other suitable mechanism. Post 188 further includes a groove at its proximal end. Preferably, a snap ring 189 may be inserted into the groove to retain the linkage on post 188. Preferably, snap ring 189 is easily removed to permit disassembly. While a snap ring has been disclosed other removable connection mechanisms may be used. It is contemplated that the linkage and guide tube may be used with multiple housings having various angulations and heights.

Figure 9:
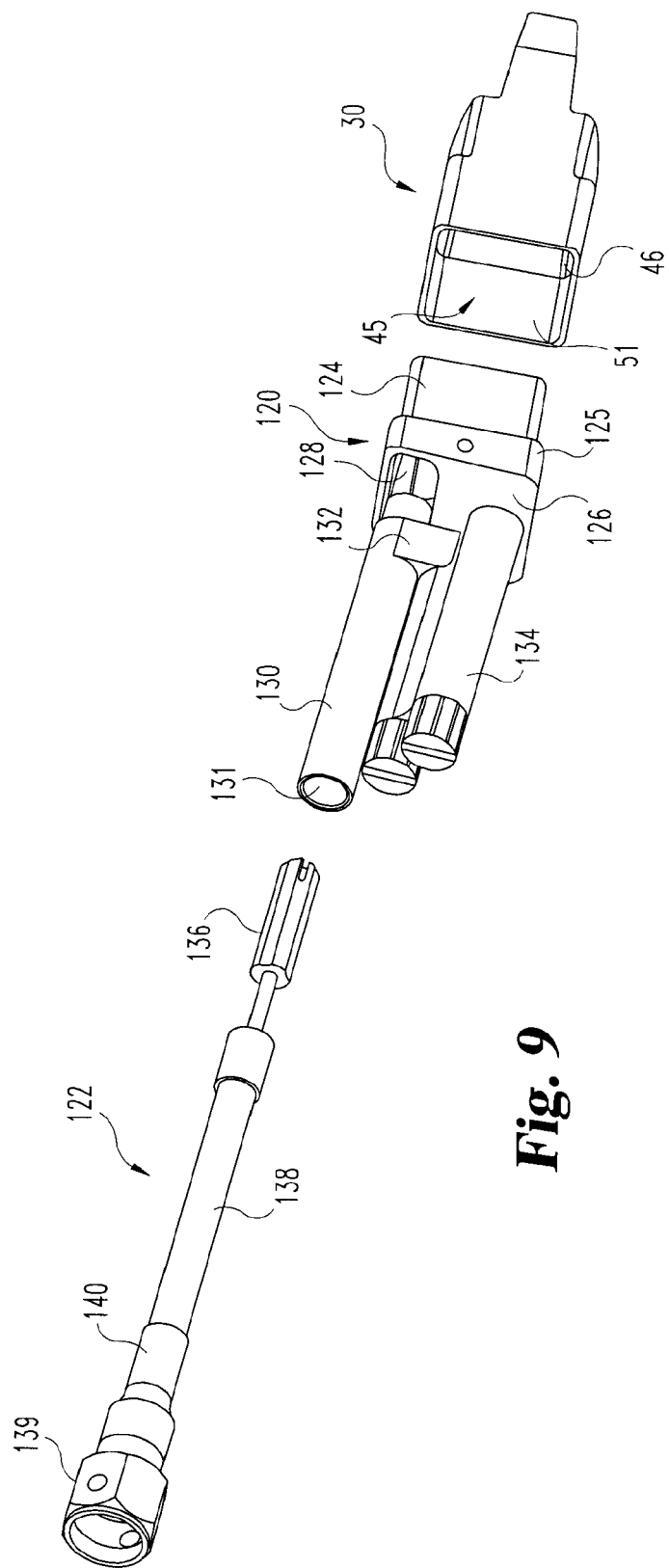
FIG. 9 is an exploded perspective view of rotary cutting guide assembly according to another aspect of the present invention.
Figure 10:
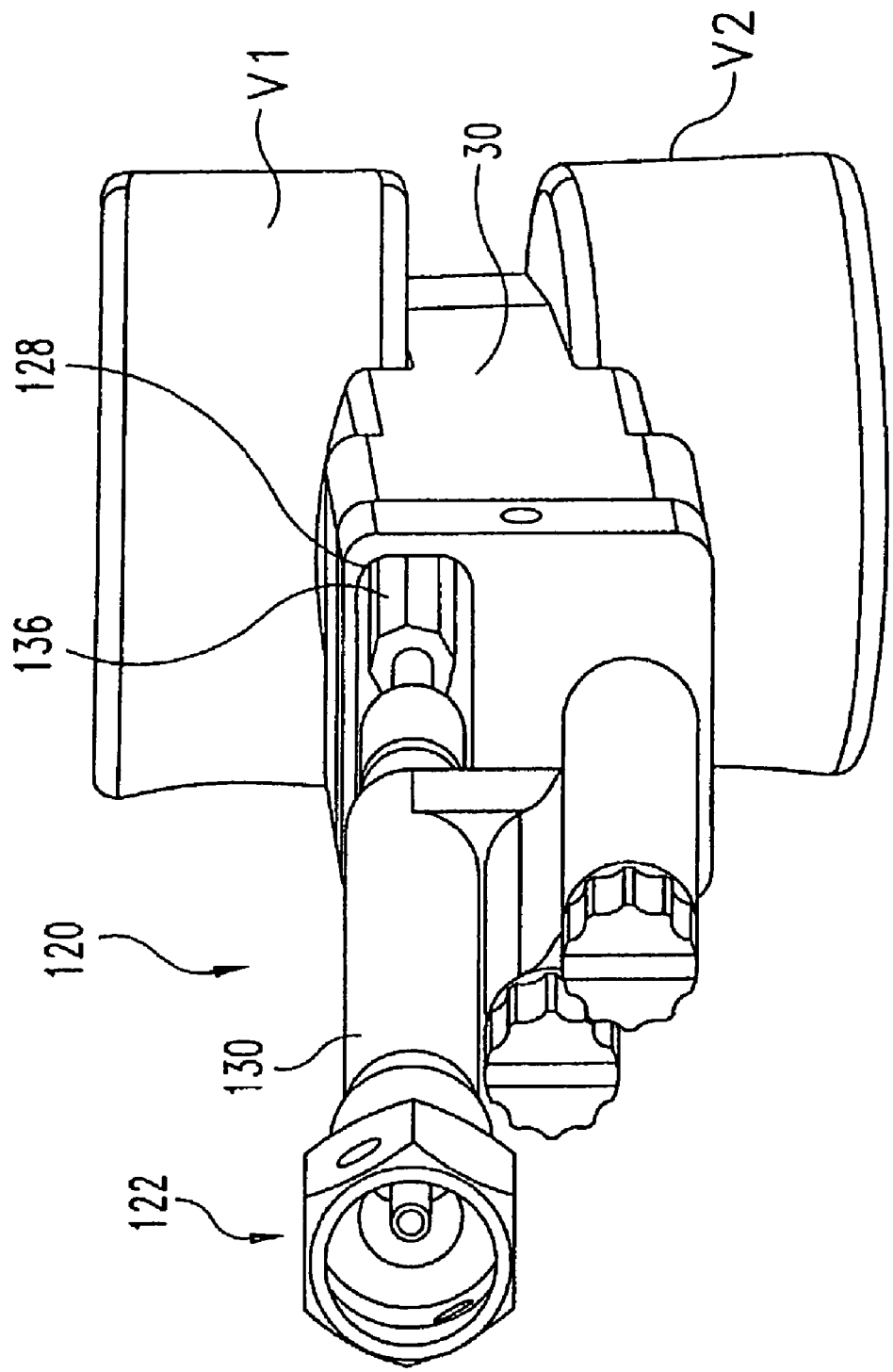
FIG. 10 is a perspective view of the rotary cutting guide of FIG. 9 in an assembled configuration.

Referring now to FIGS. 9 and 10, guide assembly 120 may be inserted into distraction window 130 with insertion end 124 securely received within distal portion 51. In a preferred embodiment a burr may be received with the cutting bit 136 extending into channel 131 and substantially beyond channel 131 with the ability to engage and cut exposed vertebral bone or other tissues. Shaft 138 is substantially received within channel 131 with large portion 140 abuttingly engaging annular flange 154 to limit the axial extent cutting instrument 122 may extend within guide 120. Shaft 138 is sized to be a snug fit within channel 131 to provide precise guiding of the cutting bit 136. In a preferred aspect, cutting instrument 122 will further include a coupler 139 for attachment to a power source to drive cutting bit 136. Only a particular cutting instrument has been shown for use with the guide of the present invention. However, it is contemplated that other alternative cutting instruments, including hand operated instruments, may be utilized in combination with the guide assembly of the present invention, it being understood that the guide assembly 120 provides controlled cutting of angular surfaces with the angle of cut being substantially maintained over a large lateral distance. Further, guide tube 130 and the accompanying linkage not only maintain the vertical angulation of the cutting instrument but also maintain the cutting instrument in a substantially fixed side-to-side angulation thereby limiting the potential for accidental penetration into tissues along the lateral extent of the disc space. More specifically, guide tube 130 maintains the orientation of cutting bit 136 substantially perpendicular both horizontally and vertically with respect to flange 129 and guide face 126.

Figure 17B:
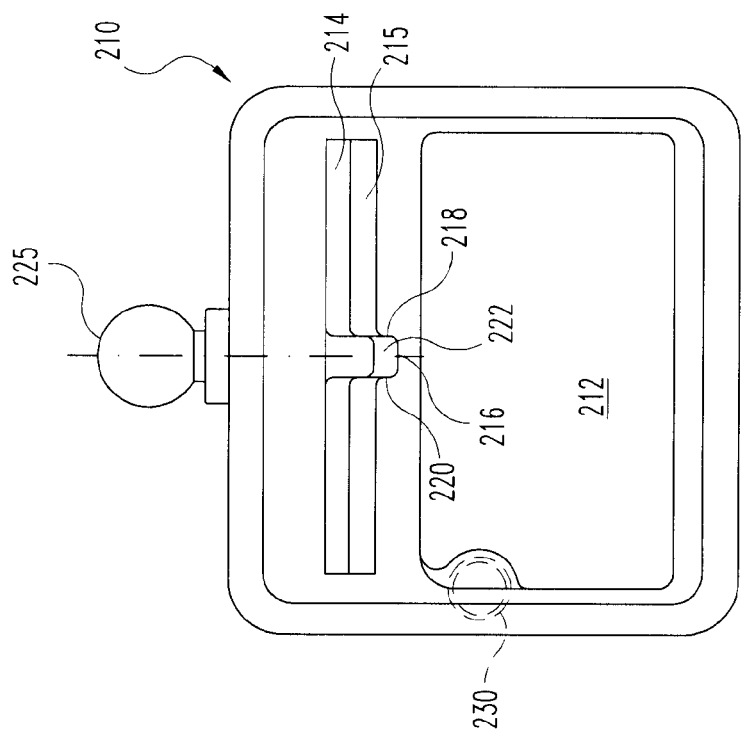
FIG. 17b is a rear end view of the guide block of FIG. 16.
Figure 17A:
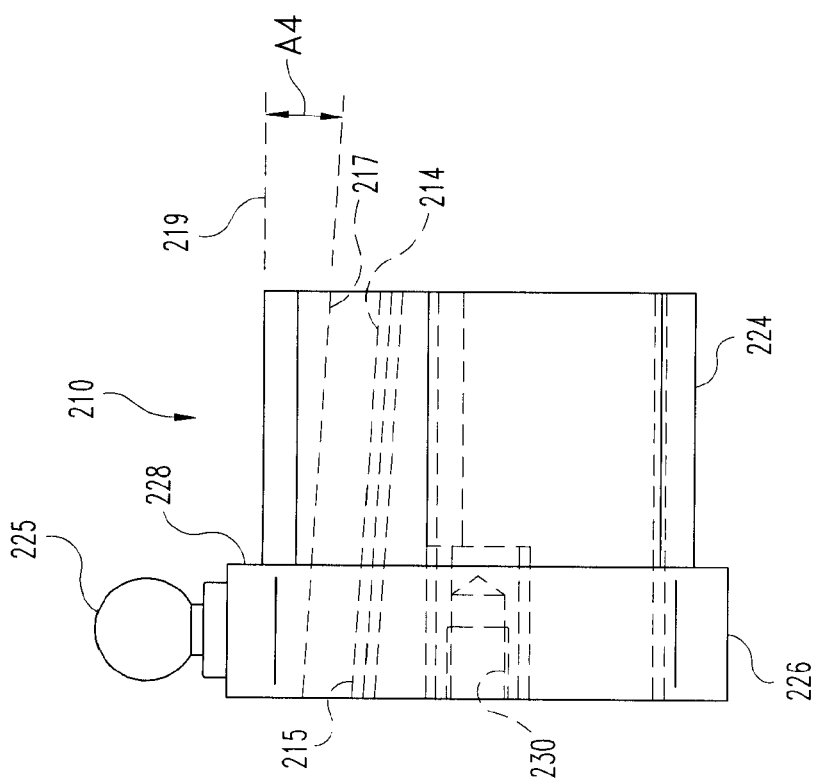
FIG. 17a is a side view of the guide block of FIG. 16.

Referring now to FIG. 16, there is another perspective view of distraction window 30 in combination with a cutting blade guide 210 and a cutting instrument 250. As previously discussed with respect to guide assembly 120, blade guide 210 includes an insertion end 224 configured for engagement with proximal portion of distraction window 30. Blade guide 210 includes a blade channel 214 defined by opposed surfaces 217 and 215. In a preferred aspect, opposed surfaces 215 and 217 are substantially parallel and extend at an angle A4 with respect to the longitudinal axis 219. In one embodiment, angle A4 is approximately 4 degrees. However, it is contemplated that angle A4 may vary between 0 degrees and 30 degrees depending on patient anatomy and the amount of bone to be removed. Blade guide assembly 210 further includes a guide channel 216 defined by opposed side walls 218 and 220 and lower guide surface 222. These surfaces also extend at an angle A4 with respect to axis 219. Guide assembly 210 also includes an internally threaded bore 230 and an enlarged external flange 226 having a surface 228 adapted to abuttingly engage the proximal edge of distraction window 30. FIGS. 17a and 17b further disclose a tooling ball 225 utilized during the manufacturing process as a reference point for manufacturing the various angled surfaces of the guide assembly. It will be understood that tooling ball 225 is preferably removed after manufacture.

Figure 18A:
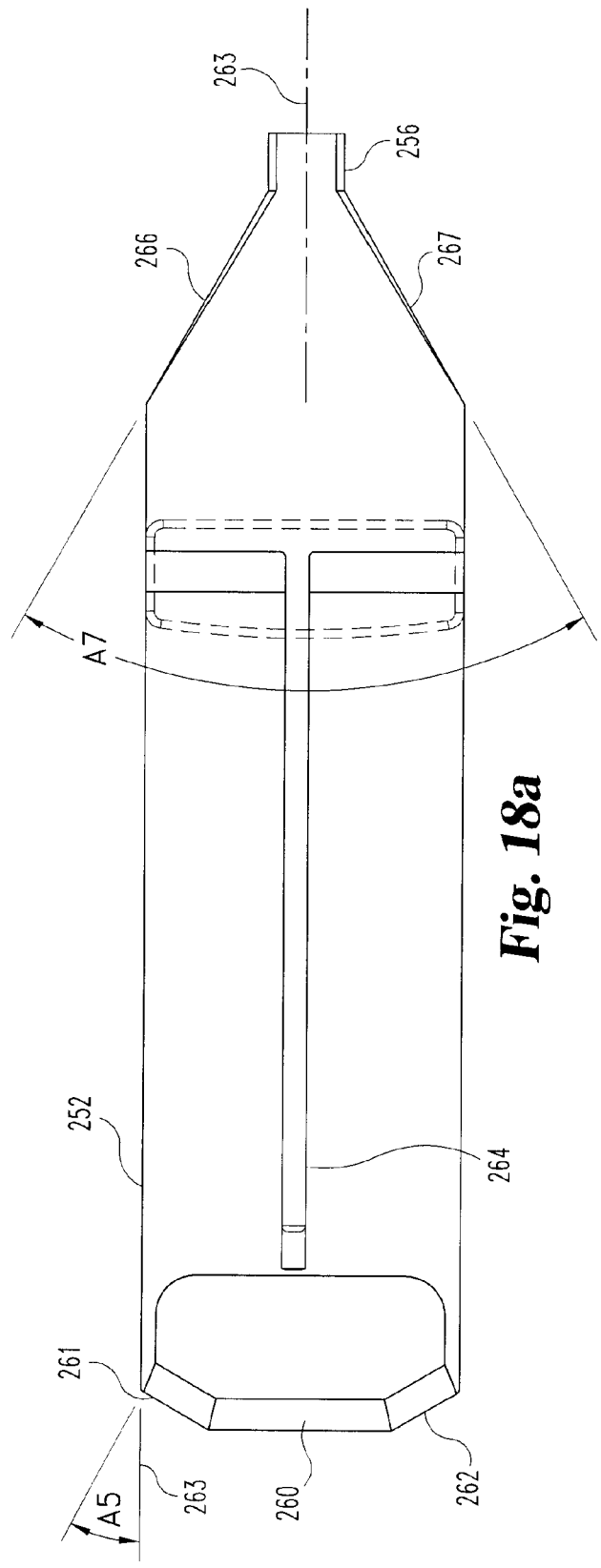
FIG. 18a is a top plan view of a chisel blade configured for use with the guide block of FIG. 16.
Figure 18B:
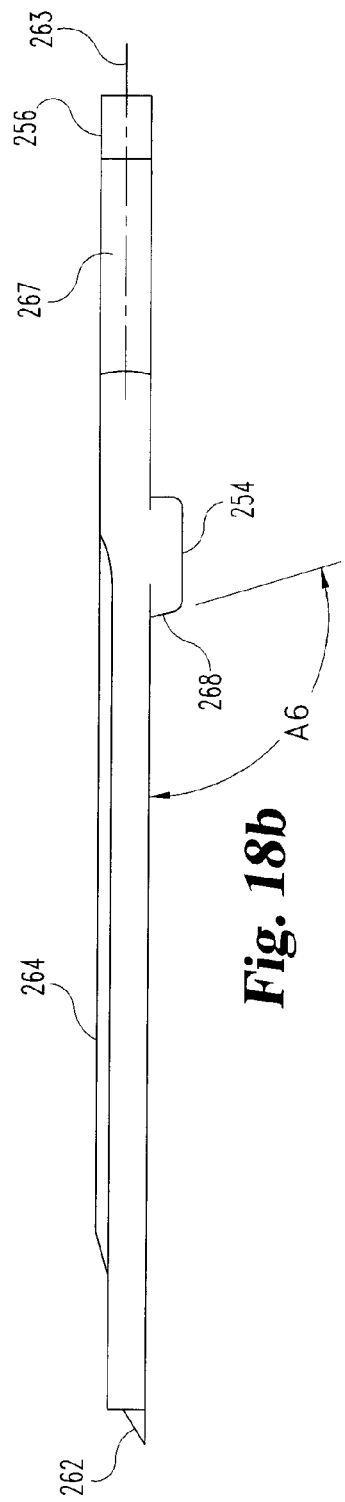

Referring now to FIGS. 18a and 18b, cutting instrument 250 includes a blade 252, a stop 254 disposed on the proximal portion of blade 252, a shaft 256 interconnected with a handle 258. Blade 252 includes a cutting blade having a first leading blade 260, a first lateral cutting blade 261, and a second lateral cutting blade 262. Cutting blades 261 and 262 are preferably set with an angle A5 with respect to the longitudinal axis 263. In a preferred embodiment, A5 is approximately 30 degrees. Blade 252 further includes guiding rib 264 extending substantially along the longitudinal axis of the blade and having a height substantially taller than the blade thickness. It will be understood that guiding rib is configured to slidingly engage guide channel 216 formed in guide housing 210. Blade 252 further includes a stop 254 having a leading face 268 disposed at an angle A6 with respect to the longitudinal axis of the blade. Preferably angle A6 is between 80 and 100 degrees in a more preferred aspect is 94 degrees. Leading edge 268 is adapted to abuttingly engage the face of housing 210 to prevent further advancement of blade 252. The trailing edges of blade 252 include tapered surfaces 266 and 267 set at an angle A7, which preferably is 60 degrees. Blade 252 is attached to shaft 256.

Referring to FIG. 16, it will be understood that as cutting instrument 250 enters guide 210 the leading elements of blade 252 engage the exposed vertebral bone (see FIG. 8) and continue at the designated angle thereby removing a portion of the vertebral end plate at the desired angular relation. Viewing window 212 of housing 210 permits the user to remove the cutting debris and view the end plate to determine if preparation has been completed.

Figure 38:
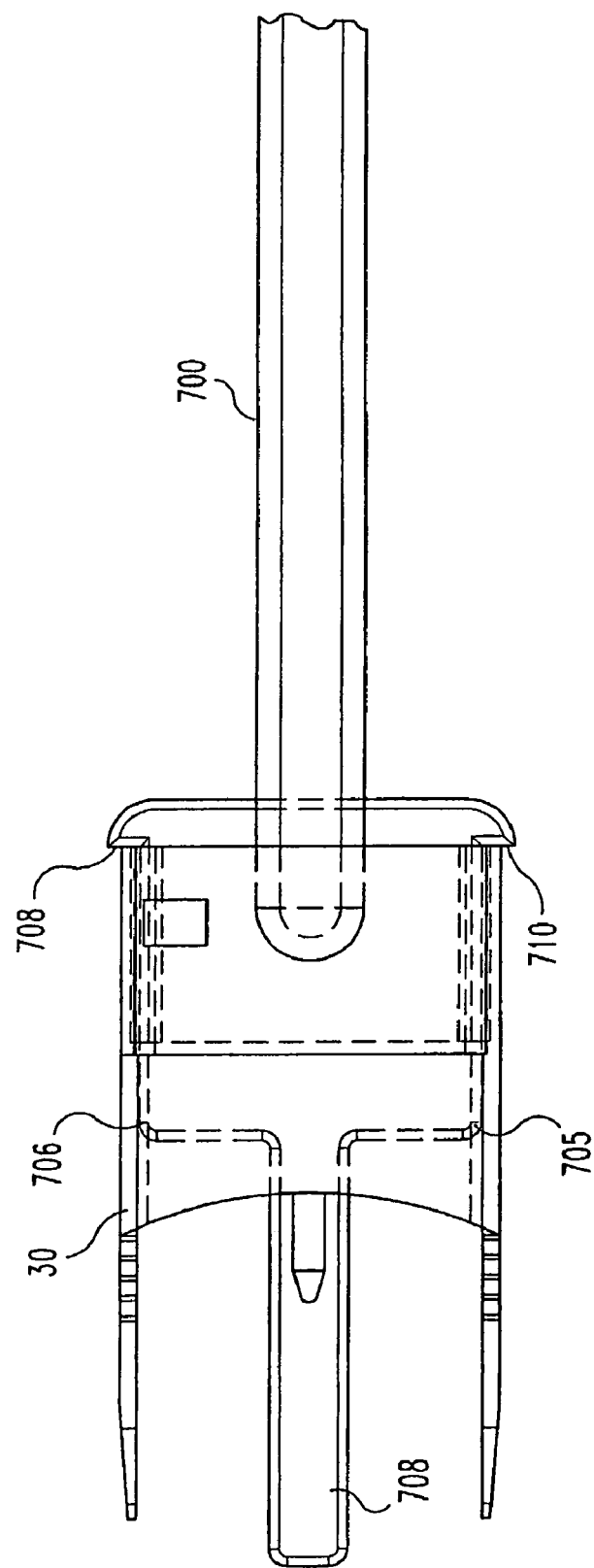
FIG. 38 is a top view of a depth gauge in combination with a distraction window according to another aspect of the present invention.
Figure 39A:
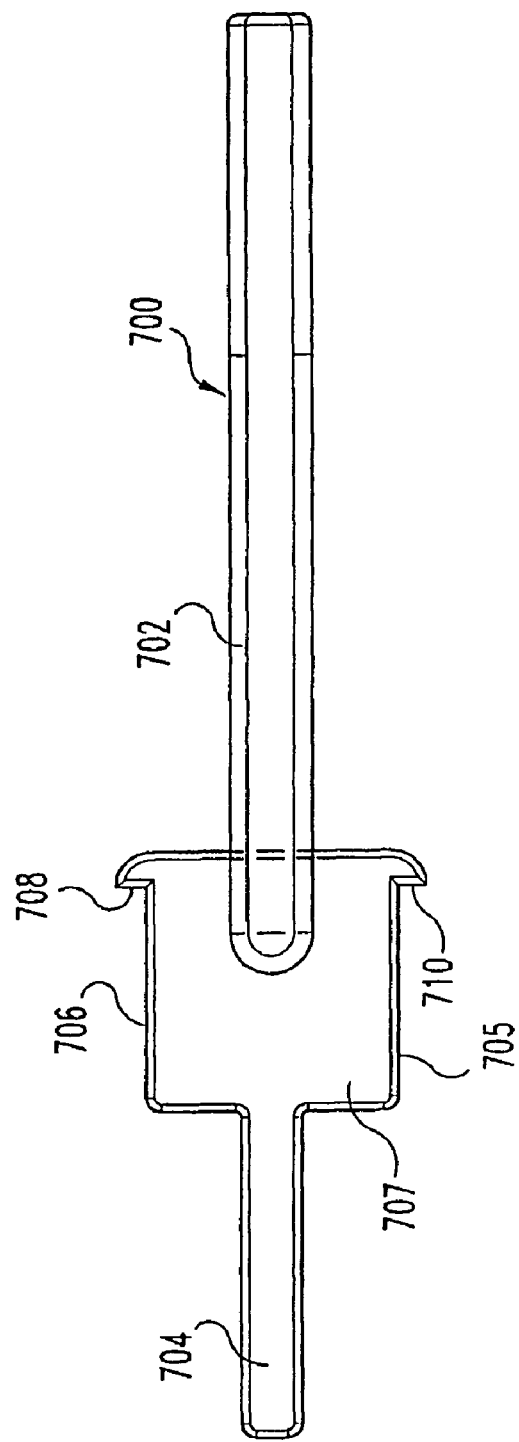
FIGS. 39a and b are a top view and side view, respectively, of the depth gauge of FIG. 38.
Figure 39B:
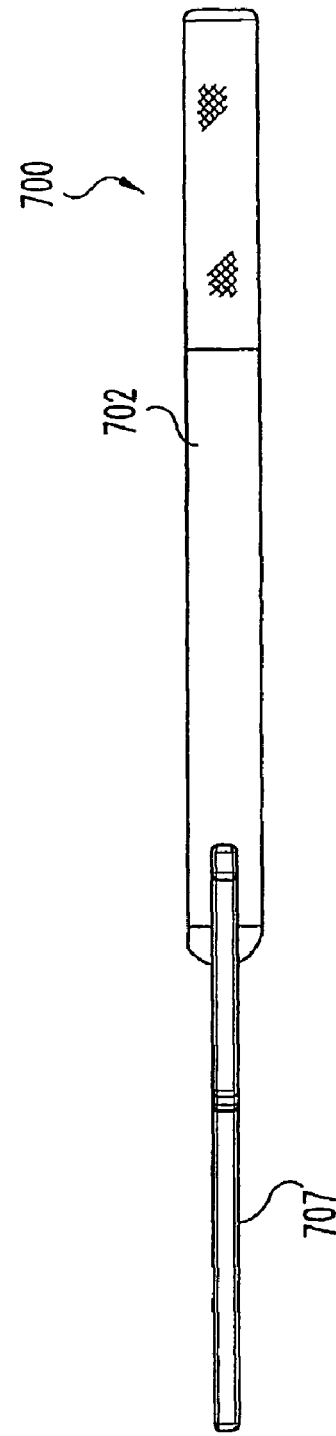

Referring to FIGS. 38 through 39b, there is shown a depth gauge according to the present invention. Depth gauge 700 includes a shaft 702 interconnected with a depth blade 707. Depth blade 707 has an elongated portion 704, wide body portion having side walls 705 and 706, and proximal shoulders 708 and 710. Referring to FIG. 38, depth gauge 700 may be inserted into window 30 and into the disc space to visually evaluate the intended depth of cut into the vertebral endplates. Side walls 705 and 706 maintain alignment in window 30 while shoulders 708 and 710 are configured to engage the proximal end of window 30 to limit further advancement. With shoulders 708 and 710 engaged with window 30, elongated portion 704 approximates the distance for a given cutter depth. It will be understood that a variety of depth gauges may be provided to approximate various depths of bone removal.

Guided end plate preparation by both rotary cutting means and cutting blades has been disclosed in the foregoing description. It will be understood that the thickness of vertebral bone removed, the angle of the cut and the side-to-side movement (if any) is precisely controlled by the design of the guides. Guides allowing varying incremental bone removal are contemplated to provide the ability to adjust endplate preparation depths without removal of the distraction window. Furthermore, controlled end plate preparation of the upper vertebral bone has been disclosed, it being understood that the guides may be rotated 180 degrees and inserted into the distraction window for substantially similar preparation of the lower end plate.

Figure 19A:
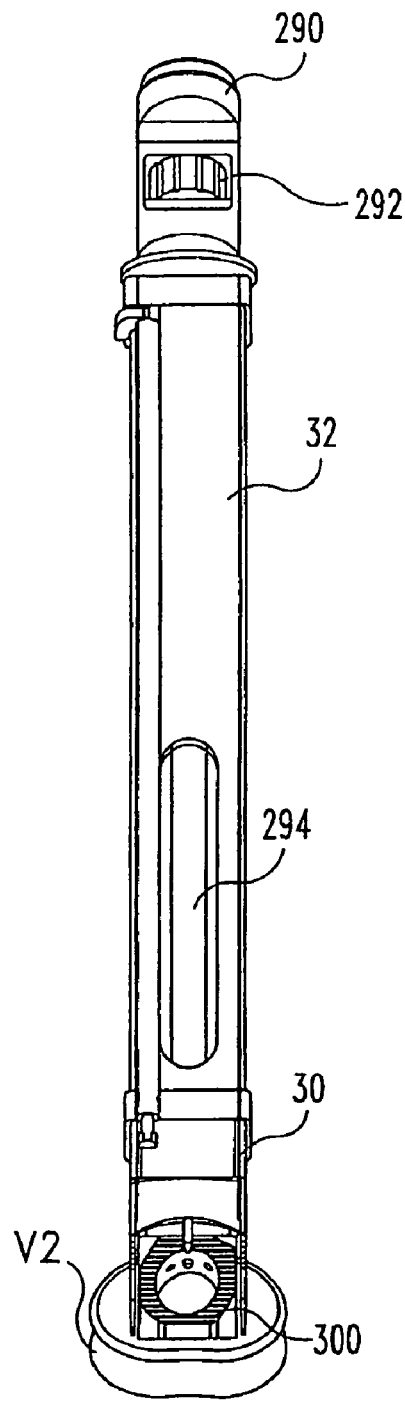
FIG. 19a is a perspective view of an implant insertion assembly disposed adjacent a vertebral body.
Figure 19B:
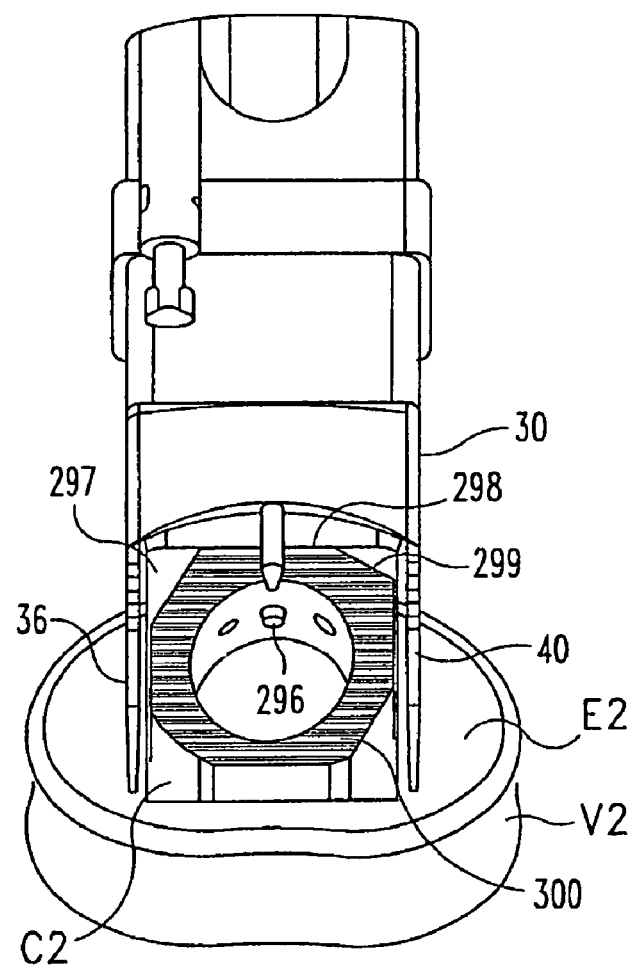

After a disc space has been prepared including removal of the desired amount of end plate bone at the desired angle, an implant may be inserted through distraction window 30. Referring now to FIGS. 19a and 19b, guide tube 32 is preferably reattached to distraction window 30 as previously described. An insertion device 290 configured for insertion, through the guide tube and distraction window may then be utilized. Insertion device 290 represents an example of such an insertion device. Implant inserter 290 includes an outer shaft 294, an inner shaft 296 having a threaded distal end and a thumb wheel 292 attached on a proximal end. The inner shaft is free to rotate within outer shaft 294. The distal end of the insertion device includes implant engaging surfaces 297, 298, and 299. It being understood that preferably surfaces 297, 298, and 299 have an angular relationship substantially matching the surface of the implant. Further descriptions of other suitable implant inserters and implants are provided in Provisional Application entitled "INSTRUMENTS AND IMPLANTS FOR MULTI-DIRECTIONAL INSERTION OF A VERTEBRAL SPACER," filed on Feb. 22, 2000, and is hereby incorporated by reference in its entirety.

Figure 20B:
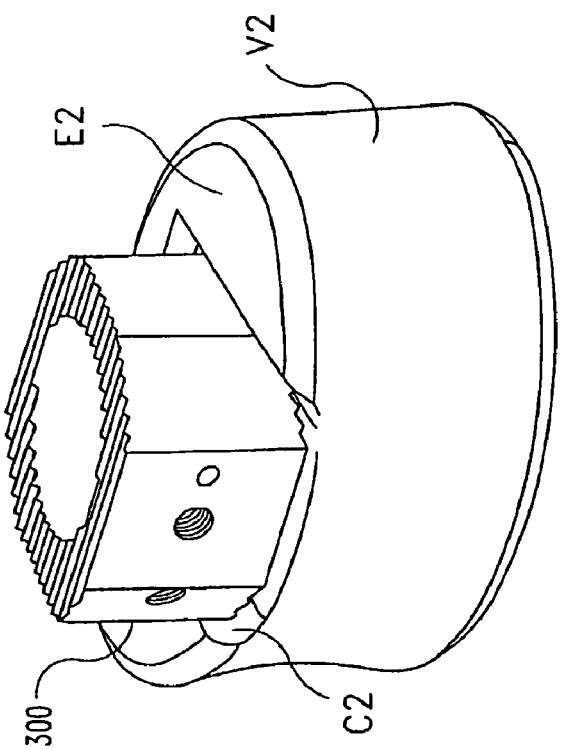
Figure 20A:
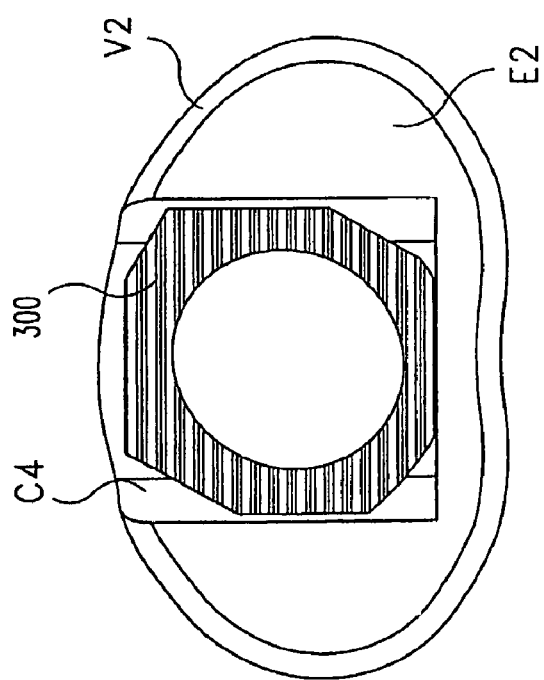
FIG. 20a is a top plan view of an implant according to the present invention disposed adjacent a prepared vertebral body.

In use, the implant includes an internal bore and thumb wheel 292 is rotated such that externally threaded internal shaft 296 engages an internal bore on the implant firmly positioning the implant against the implant engaging surfaces 297, 298, and 299. The implant and inserter advance through the guide tube 32 and through distraction window 30 until the implant is positioned in channel C2 prepared an end plate E2 of vertebra V2 and a corresponding channel of the end plate of the upper opposed vertebra. Implant 300 is retained in position between distraction holding members 36 and 40 in the prepared disc space. In a preferred aspect, implant 300 is entirely disposed within the boundaries of vertebra V2 and is oriented to maintain proper angulation between adjacent vertebral bodies. The relationship of implant 300 with respect to vertebra V2 is shown more clearly in FIGS. 20a and 20b.

Referring to drawing FIGS. 21-39c, there are disclosed instruments and techniques for approaching the spine from an anterior-oblique direction. With respect to patient anatomy, the spine is approached in substantial alignment with the axial plane and at an oblique angle with respect to the sagittal plane. It is believed that precision guided techniques and instrumentation for an oblique-anterior approach to the spine have not been previously available.

Figure 21:
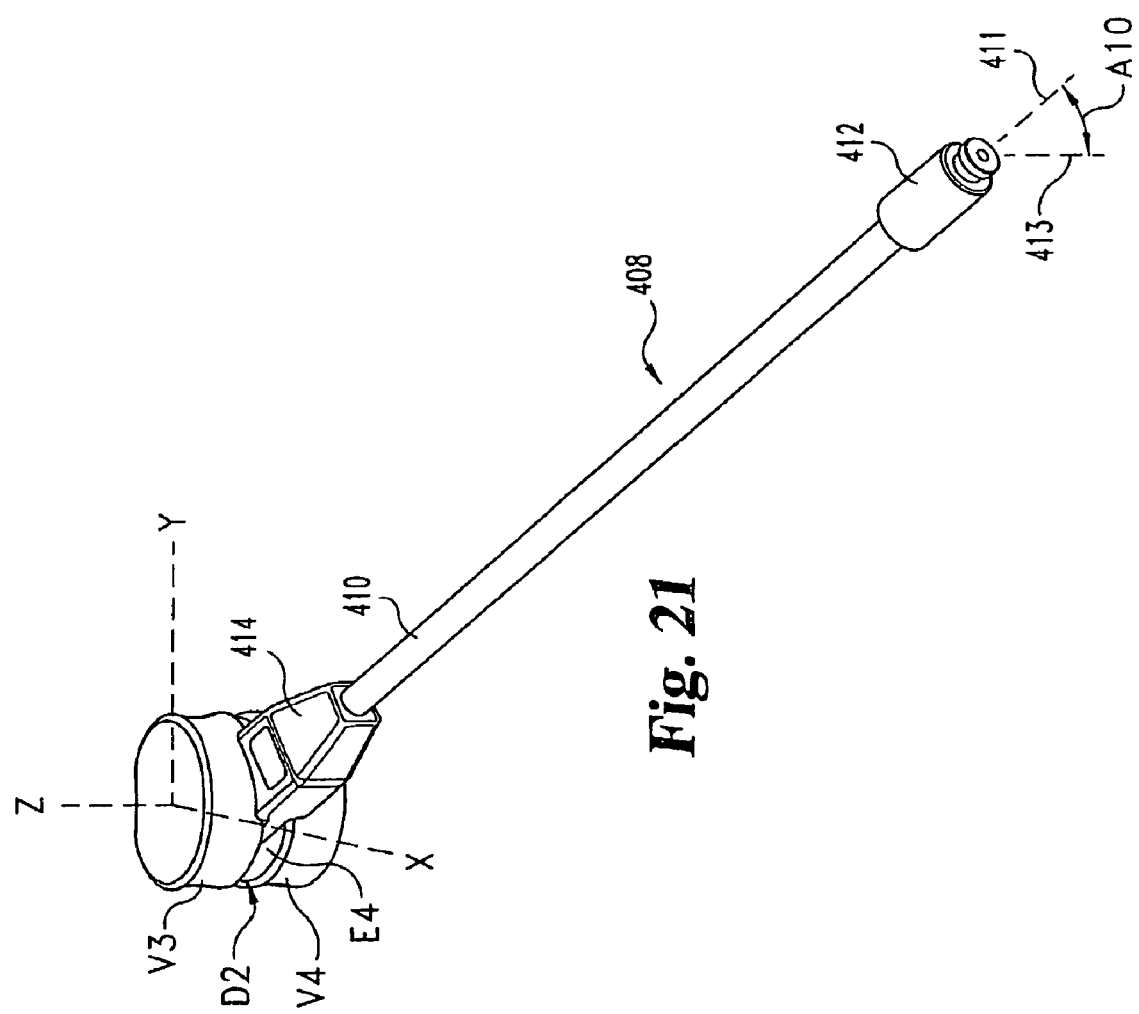
FIG. 21 is a perspective view of a distractor disposed between two adjacent vertebral bodies from an oblique anterior approach to the spine.

Referring specifically to FIG. 21, a portion of the spine including two adjacent vertebrae V3 and V4 are shown with disc space D2 disposed between the adjacent vertebrae. The vertebrae are shown in a perspective view from a substantially anterior perspective. As the XYZ coordinate system illustrates, the X coordinate comes substantially out of the paper, the Y coordinate extends from left to right, and the Z coordinate extends from top to bottom of the drawing FIG. 21. A distractor 408 is shown disposed in disc space D2 and is oriented in the disc space along longitudinal axis 411. Reference line 413 is drawn substantially parallel to X-axis and forms an angle A10 with longitudinal axis 411. While it is contemplated that an oblique approach to the spine may be made at a variety of non-orthogonal angles, in a preferred aspect of the invention angle A10 is approximately 30 degrees.

Distractor 408 includes elongated shaft 410, a tool engaging end 412 adapted to engage a driving or retrieval tool and a distraction head 414 disposed on the distal end of shaft 410. Distractor 414 includes a centering block 422 and inclined surfaces on the proximal portion tending to align a guide sleeve with centering block 422. With respect to drawing FIGS. 23a-23e a tool ball 452 is shown. The tool ball 452 is utilized during the manufacturing process to insure proper alignment for the various machining operations. It is contemplated that the tooling ball will be removed from the finished product after the manufacturing process is substantially complete.

Figure 23D:
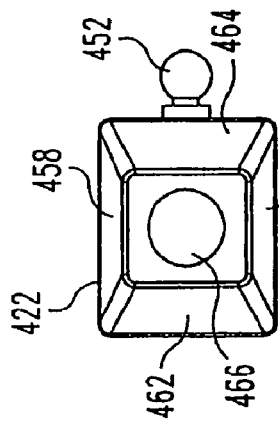

Referring now to FIGS. 23a-e, the centering block 422 incline surfaces include upper surface 458 and opposed lower surface 460 combined with opposing side surfaces 462 and 464. Distraction head 414 further includes a leading edge 440 and an angled leading edge 442. As shown in FIG. 23a, angled leading edge 442 is disposed at an angle A12 with respect to leading edge 440. In a preferred embodiment, angle A12 is approximately 30 degrees corresponding to the oblique angle of approach to the anterior spine. Adjacent leading edge 440, distraction head 414 has a top tapered surface 434 and a bottom tapered surface 432. Similarly, adjacent angled leading edge 442 there is a top tapered and angled surface 438 and a bottom angled tapered surface 436. Angled surfaces 438 and 436 are formed in a plane extending substantially 30 degrees with respect to similar surfaces 434 and 432. Top tapered surfaces 434 and 438 lead to upper distraction surface 444 while lower tapered surfaces 432 and 436 lead to lower distraction surface 446. Upper distraction surface 444 terminates into upper bone engaging surface 428. In a similar manner lower distraction surface 446 terminates in bone engaging surface 426. Bone engaging surface 428, and in a similar fashion lower bone engaging surface 426, are defined by a concave arcuate surface based on an off center radius of curvature. Specifically, upper bone engaging surface 428 has a leading edge 468 extending more distally than trailing edge 470. In a preferred aspect, leading edge extends substantially 6 mm more distally than trailing edge 470.

As shown in FIG. 23a, a slot 448 is formed through the leading portion of distraction head 414. Slot 448 is offset from side wall 456 by distance D10 and is offset from opposing side wall 454 by distance D11. In a preferred aspect, distance D10 is greater than distance D11 resulting in slot 448 being substantially off center with respect to the centerline of distraction head 414. A guiding fin 430 having a height greater than corresponding portions of distraction head 414 may be disposed in slot 448 and held in position by pins 450 extending there through. Guiding fin 430, shown in FIGS. 22a-c, is adapted to engage the vertebral bone and cut a guiding channel through the bone to maintain the proper direction of distraction head 414 during the insertion process. Still further, a bore 466 is formed in the rear of distraction head 414 and is utilized for interconnection with shaft 410.

Figure 23E:
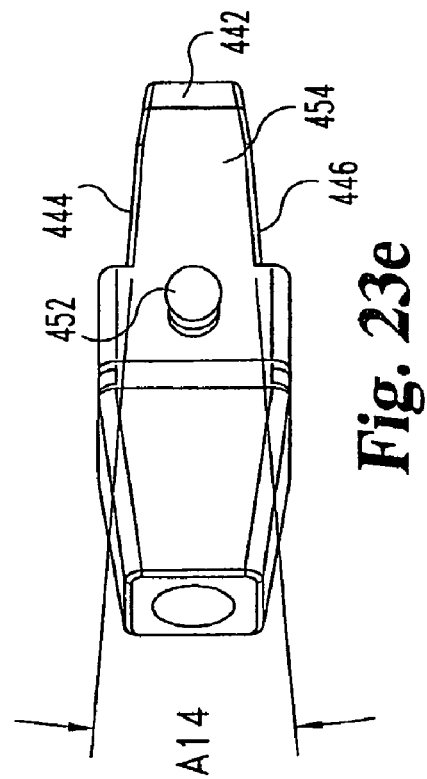
Figure 23C:
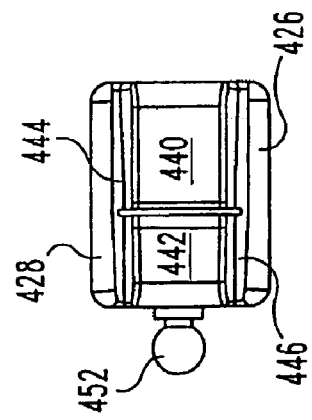

It is contemplated that instruments according to the present invention may be utilized from an anterior-oblique approach for distraction on the vertebra having a non-parallel angular relationship. In this instance, establishing and/or maintaining the appropriate angular relationship between adjacent vertebra must be considered when approaching the disc space from an oblique angle. Thus, in one aspect of the preferred embodiment, upper distraction 444 and lower distraction surface 446 are disposed at an angle approximating the desired angular relationship of the vertebral disc space. While such angulation may vary from 0 degrees to 20 degrees throughout the spine, particular angles of 4 degrees to 12 degrees of angulation are often encountered in lumbar spinal applications. The angular relationship of the upper distraction surface 448 and lower distraction surface 446 is best shown in FIG. 23e and is indicated by angle A14. In this embodiment, A14 is approximately 8 degrees. FIG. 23e is a side view of FIG. 23a looking at an angle of approximately 30 degrees with respect to longitudinal axis 451. Thus, angulation A14 between the upper and lower distraction surfaces is oriented at approximately a 30 degree angle with respect to the longitudinal axis of the device such that as the instrument is inserted into the disc space from an oblique approach, the appropriate posterior to anterior angulation of the vertebral end plates may be accomplished.

Figure 24:
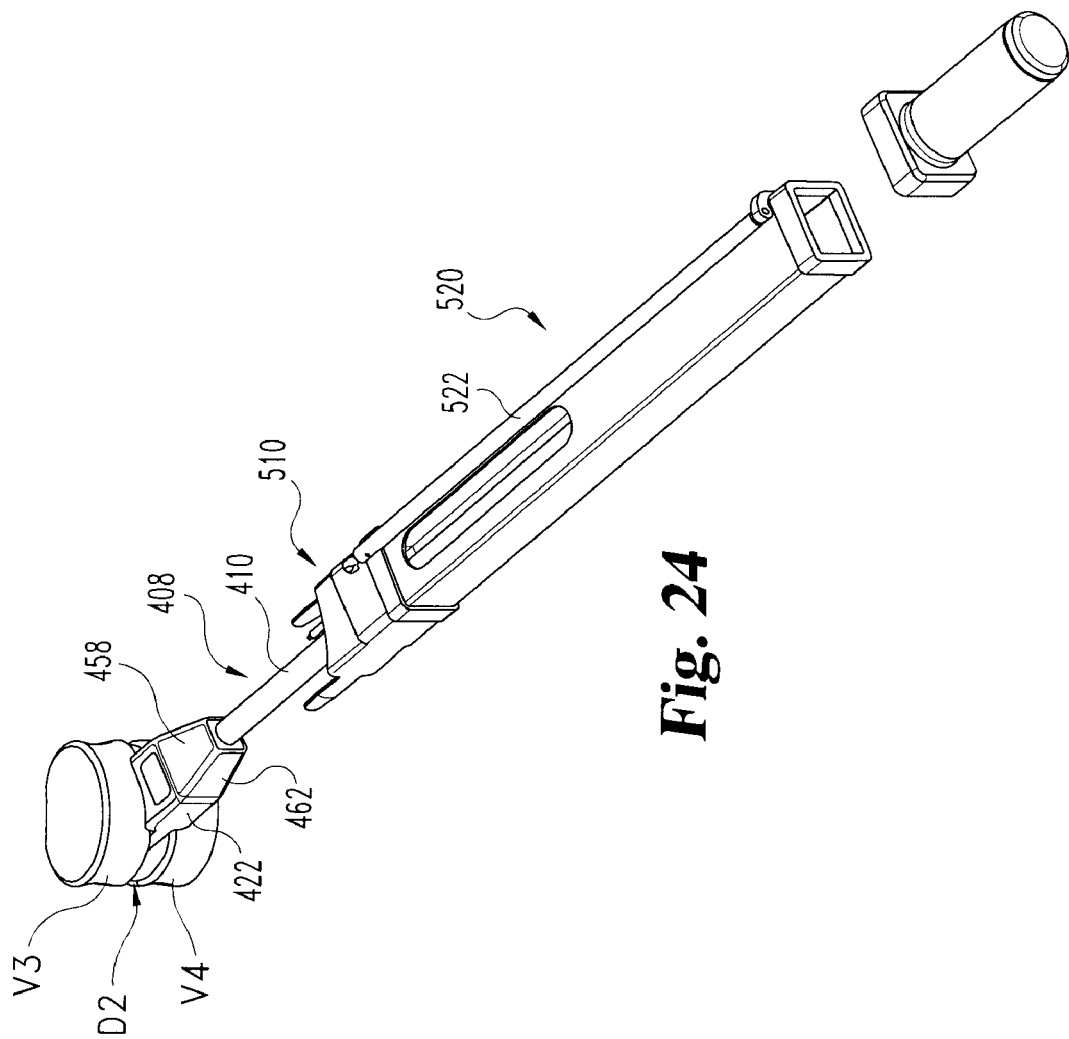
FIG. 24 is a perspective view of a distractor and guide tube assembly according to a preferred aspect of the present invention.
Figure 25:
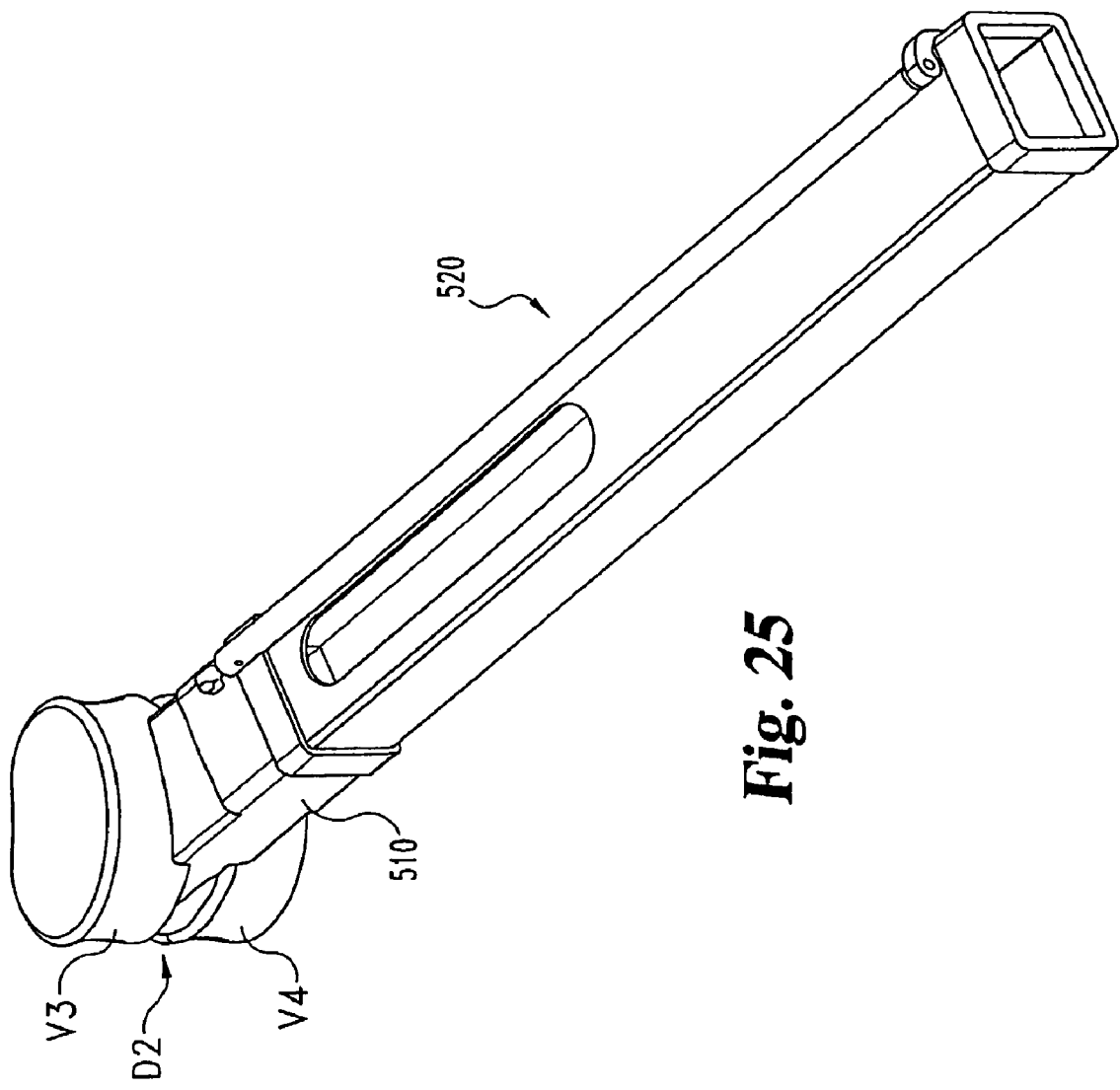
FIG. 25 is a perspective view of the guide tube assembly of FIG. 24 disposed between adjacent vertebrae.
Figure 26:
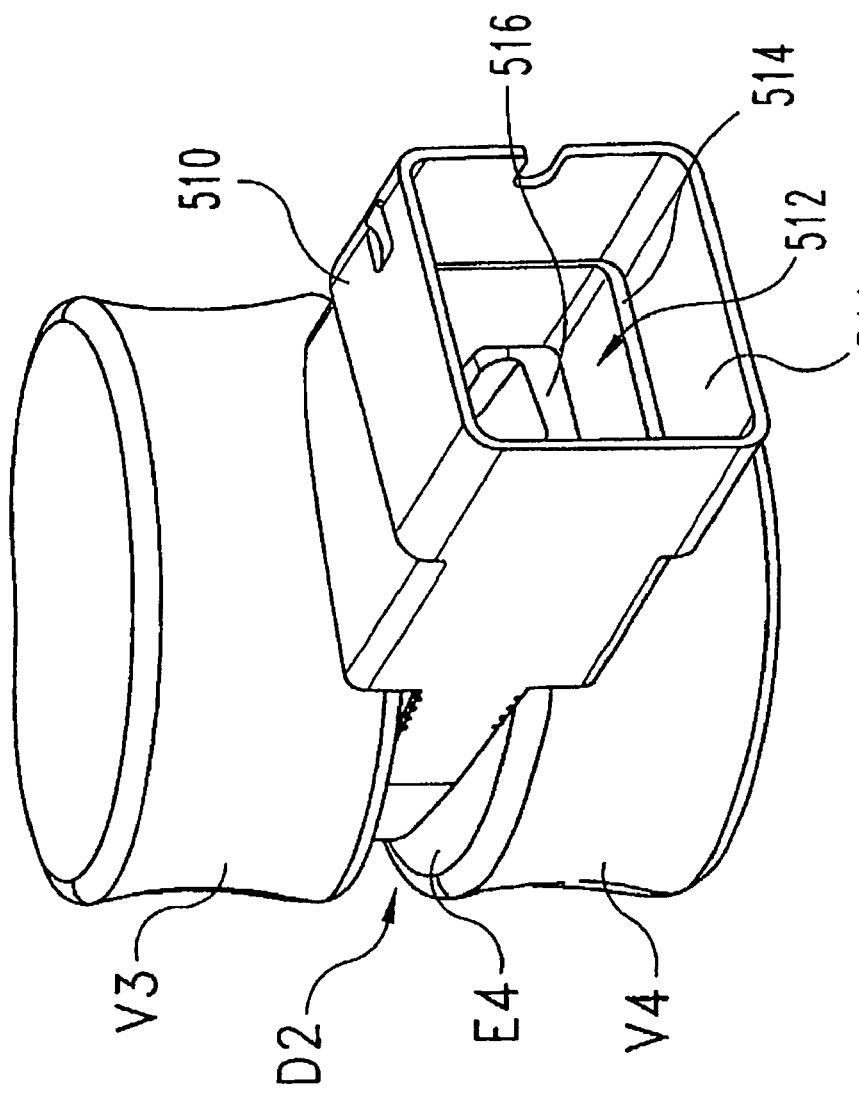
FIG. 26 is a perspective view of the distraction window of FIG. 25.

Referring now to FIG. 24, a guide tube 520 and distraction window 510 coupled by a locking mechanism 522 may be slidingly advanced along distractor 408. The locking mechanism 522 between guide tube 520 and distraction window 510 is similar to that previously discussed with respect to the embodiment shown in FIG. 3 and will not be further described herein. As shown in FIG. 26, guide tube 520 may be removed to gain access to the disc space D2 and end plate E4 at portion 516.

Figure 27D:
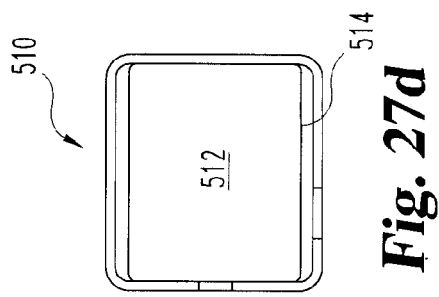
FIG. 27a through 27e are side, top, perspective, rear end, and front end views, respectively, of the distraction window of FIG. 26.
Figure 27C:
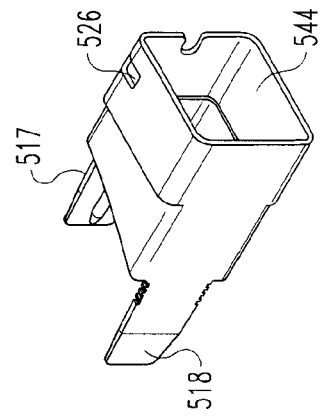
Figure 27A:
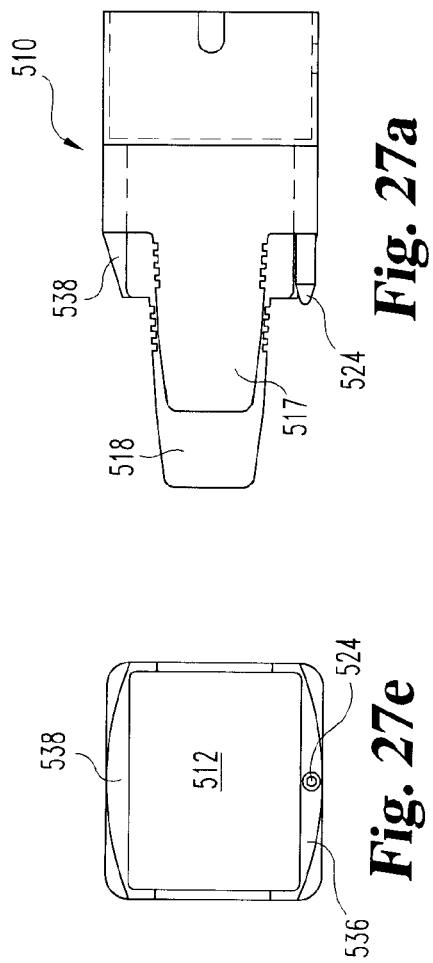
Figure 27B:
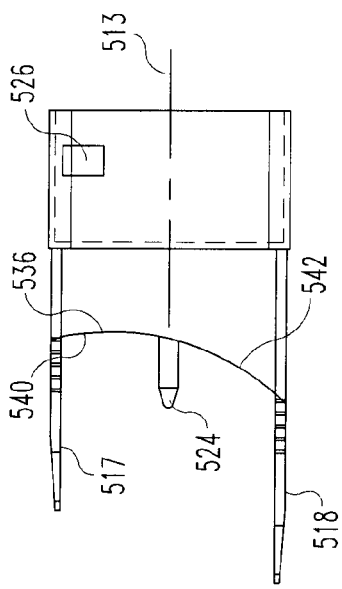
Figure 27E:
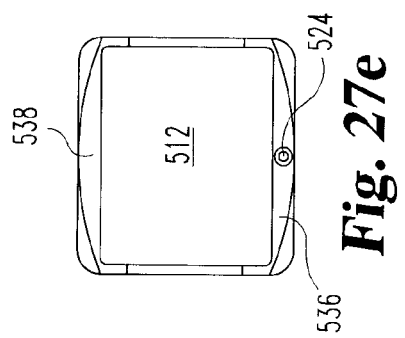

Referring to FIG. 26, distraction window 510 defines an interior working channel 512 separated into a distal portion and a proximal portion 544 by internal flange 514. Distraction window 510 includes distraction projections 518 and 517 disposed on opposite sides of the device. Distraction projections 518 and 517 when adapted for use with lordotic angulation include a taper corresponding to the angle of distractor 408 oriented at a 30 degree angle with respect to the longitudinal axis 513. Further, distraction window 510 includes upper bone engaging surface 536 and lower bone engaging surface 538, each having a concave engagement surface with an offset radius of curvature. The bone engaging surfaces 536 and 538 are adapted to engage the anterior portions of the upper and lower vertebrae respectively. As shown in FIG. 27b, upper bone engaging surface includes a leading portion 542 and a trailing portion 540. Leading portion 542 extends approximately 6 mm more distally than trailing portion 540 in a preferred embodiment. The extent that leading portion extends beyond the trailing portion depends on the oblique angle selected for access to the spine, the width of the window and the size of the vertebra to be engaged. Preferably, upper bone engaging surface 536 includes a spike 524 for projecting into the upper vertebral body. As previously described, distraction window 510 includes a recess 526 for engaging a locking mechanism of guide tube 520.

Figure 28:
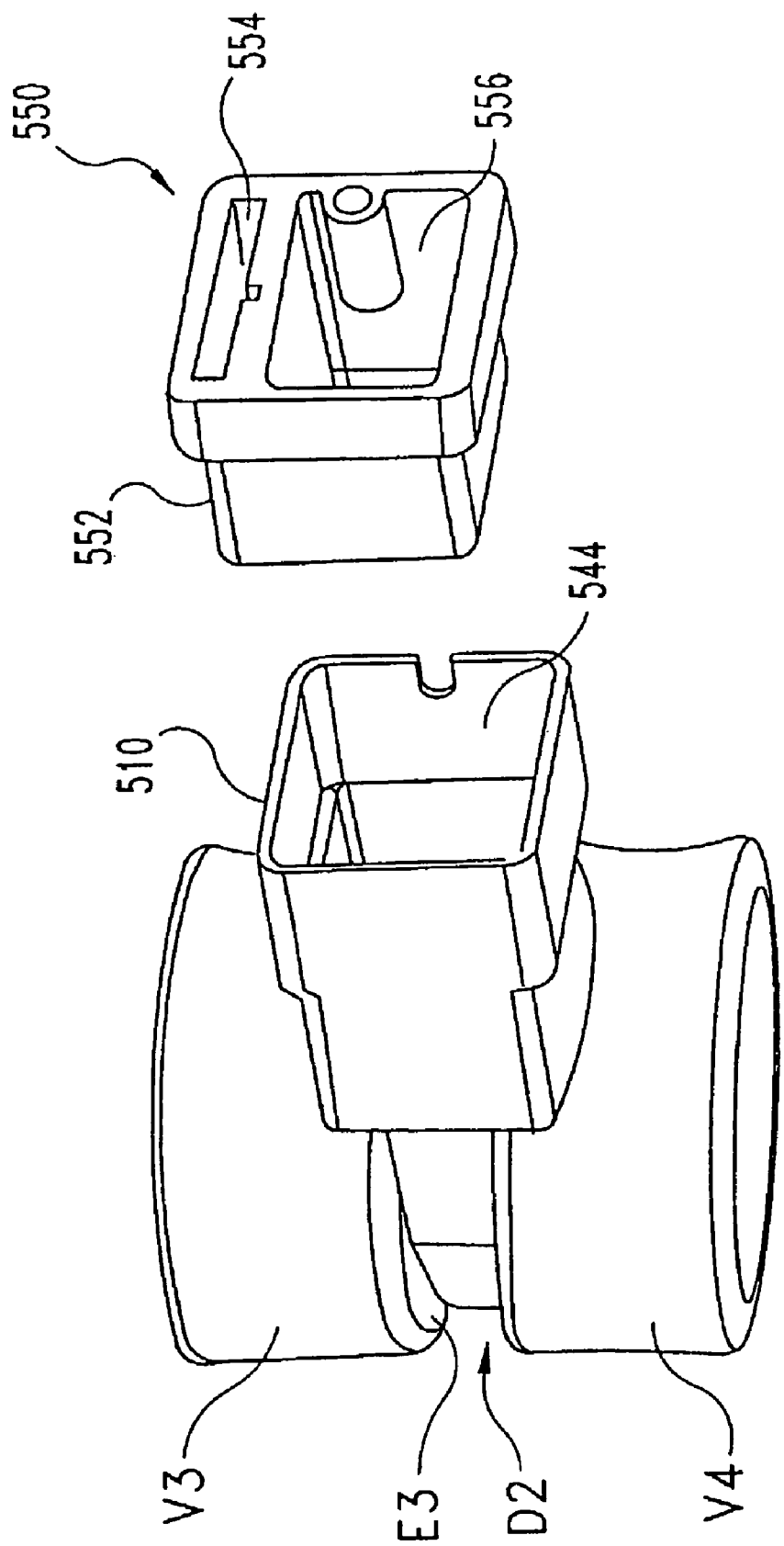
FIG. 28 is a perspective view of the distraction window and a guide block according to another aspect of the present invention.

Referring now to FIG. 28, there is shown the distraction window 510 disposed between vertebra V3 and vertebra V4. A guide block 550 having an insertion end 552 configured for engagement with proximal end 544 is also disclosed therein. The details of guide block are more fully shown in FIGS. 30a-c. Guide block 550 defines a blade guide 554 having an upper surface 668 and a lower surface 666. Specifically, the blade guide includes a guide channel 570 defined by a lower surface 588 and two opposed side walls 592 and 594. Guide block 550 further includes a visualization and working channel 556. Blade guide 554 proceeds at an angle from the front 557 to the back 559 at an angle of A13. Referring specifically to FIG. 30a, reference line 572 represents a line substantially parallel to the longitudinal axis of the guide lock and reference line 574 extends in a line substantially parallel to blade guide 554. Reference lines 572 and 574 are disposed at an angle of A13. In a preferred aspect, A13 may be approximately 3.5 degrees, however other angulations are contemplated as may be desired depending on the anatomy of the spinal segment being treated.

Blade guide 554 is also oriented at an angle extending from side 561 to 563. Referring now to FIG. 30c, a front view of FIG. 30a viewed at an angle of approximately 3.5 degrees. Reference line 562 is substantially parallel to the top surface 569 of block 550. Reference line 564 is substantially parallel to upper and lower surfaces 668 and 666, of blade guide 554. Reference lines 562 and 564 are disposed at an angle A17. In one preferred aspect, A17 is substantially 2 degrees. In another preferred aspect, reference angle A17 is substantially 4 degrees. Other angles of side-to-side angulation are contemplated and will depend on the particular anatomy of the spine to be addressed. Thus, blade guide opening 554 is set at a compound angle including a front-to-back angulation and a side-to-side angulation. Guide block 550 further includes an internally threaded bore 578 adapted to receive a portion of a handle to hold the guide block. As with previous described embodiments, a tooling ball 560 is provided to provide a reference point for creating the various compound angle surfaces. The reference ball 560 is intended to be removed once the manufacturing process is substantially complete.

Figure 31C:
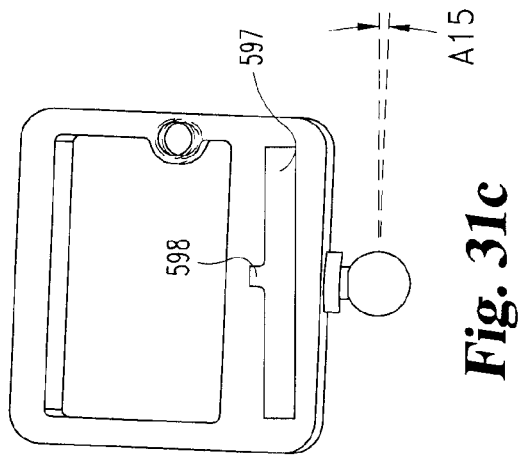
Figure 31A:
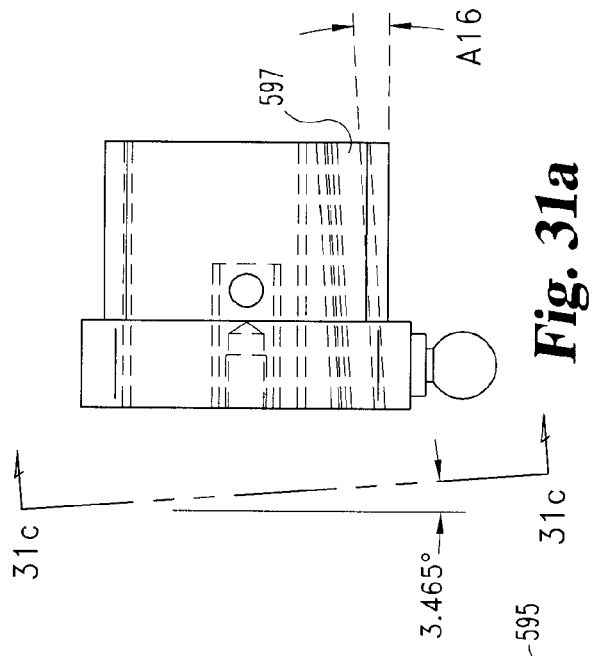
FIG. 31a is a side view an alternative guide block.
Figure 31B:
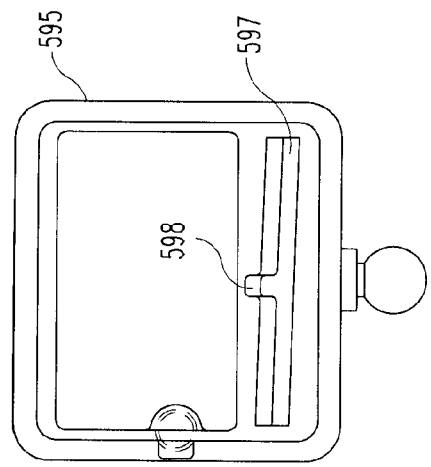

Referring to FIGS. 31a-31c, guide block 595 is provided for preparing the bottom end plate. Guide block 595 is substantially a mirror image of guide block 550 and includes a blade guide opening 597 and guide channel 598 having angulation resulting in substantially mirror image guide blade slot when compared to guide block 550. The angle of guide blade from front to back is represented by A16 and is approximately 3.5 degrees. The angulation from side-to-side is represented by angle A15 and is approximately 2 degrees in a preferred embodiment shown in drawing FIG. 31c.

Referring now to FIG. 33, a cutting blade 586 is shown for utilization with the upper guide block shown in FIG. 30a-c. Guide blade 586 includes a guiding rib 610 extending above the surface of the guide blade. Guide rib 610 is adapted to be received within guide and channel 570. Blade 586 further includes a leading cutting edge 616, a large angled cutting edge 618, and a smaller cutting edge 620. Angled cutting edge 618 and 620 extend at a substantially 30 degree angle with respect to cutting edge 616. Large angled cutting edge 618 is approximately 3 times longer than cutting edge 620. A lower cutting blade or chisel (not shown) having substantially the mirror image of chisel 586 is provided for use in lower guide block 595 to prepare the lower vertebral endplate for receiving an implant. The lower cutting blade includes a guiding rib that is offset from the center line such that it will not fit in the upper guide block. Similarly, the lower guide block has a guiding channel that is offset from center line such that it may receive the lower cutting blade guide rib but not the upper cutting blade guide rib.

Figure 40:
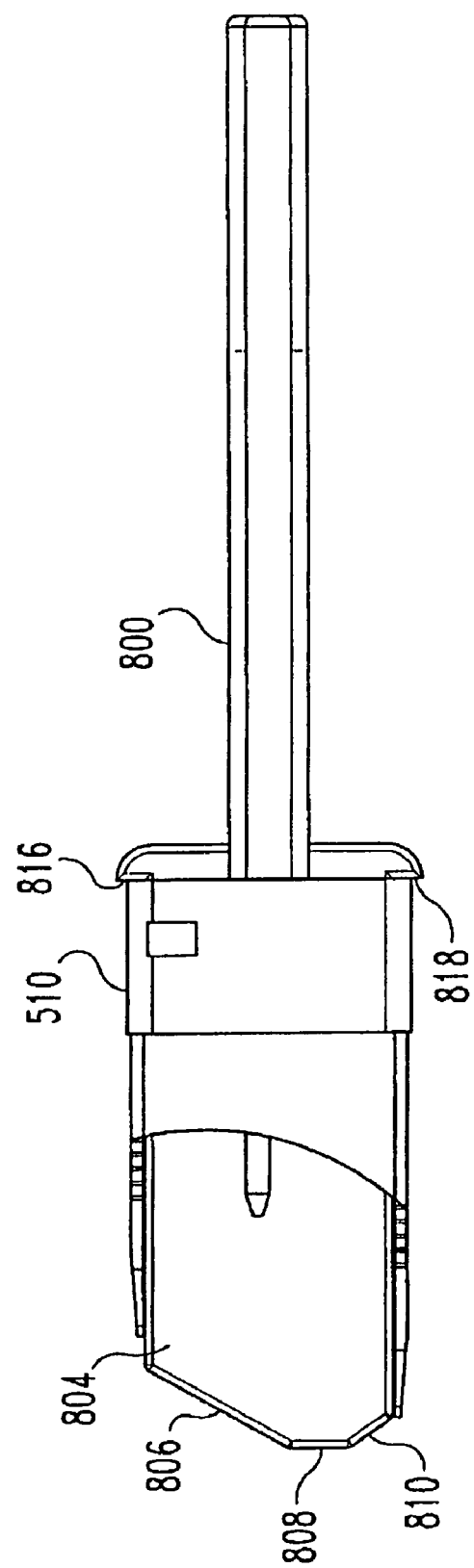
FIG. 40 is a top view of a depth gauge in combination with a distraction window according to another aspect of the present invention.

Referring to FIGS. 40 through 41b, there is shown a further depth gauge suitable for use in the oblique approach to the spine. Depth gauge 800 includes a shaft 802 interconnected with a blade 804. Blade 804 includes leading edges 806, 808, and 810 approximating the geometry of the cutting edges of the chisels previously described. Blade 804 has a width defined by side walls 812 and 814. Shoulders 816 and 818 are formed on the proximal end of blade 804. Referring now to FIG. 40, blade 804 may be inserted into window 510 to evaluate the area of cut that will be performed with a particular dimension of chisel. Blade 804 may be guided laterally be engagement of side walls 812 and 814 with portions of window 510 and longitudinally by engagement of shoulders 816 and 818 with the proximal end of window 510. In this position, the surgeon may evaluate visually, through x-ray, or any other means, the area of bone intended to be removed. It will be understood that various length blades 804 may be provided to approximate various length chisels.

Figure 34A:
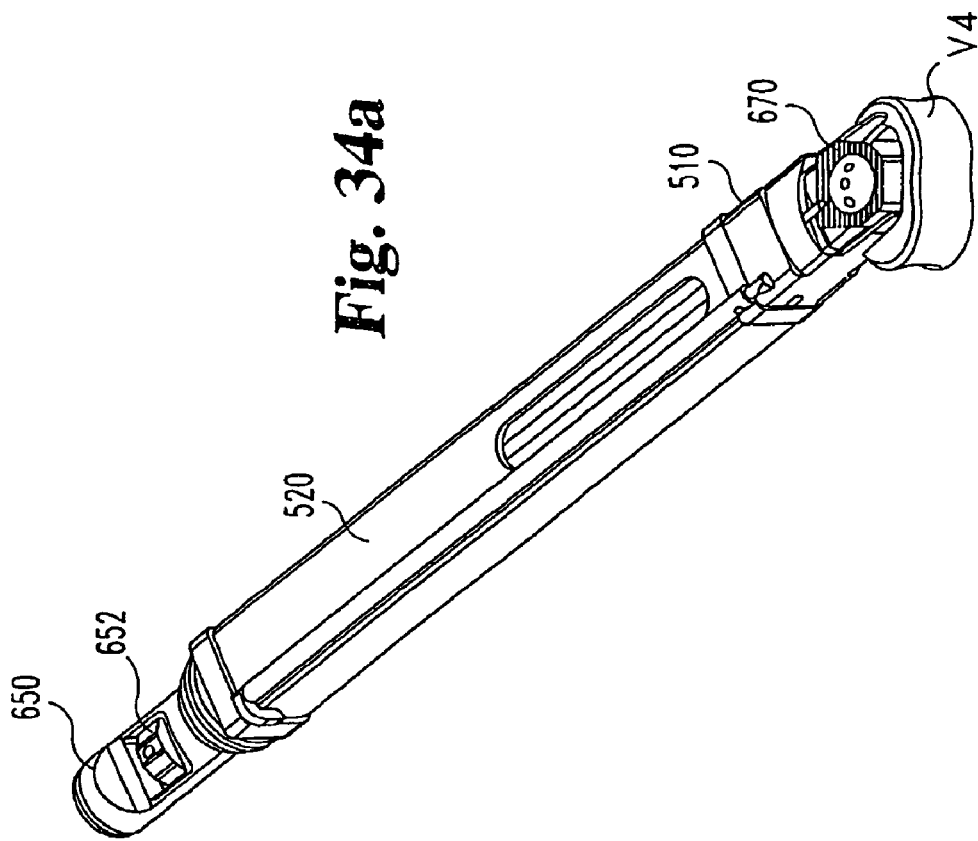
FIG. 34a is a perspective view of a guide tube and implant inserter according to the present invention.
Figure 34B:
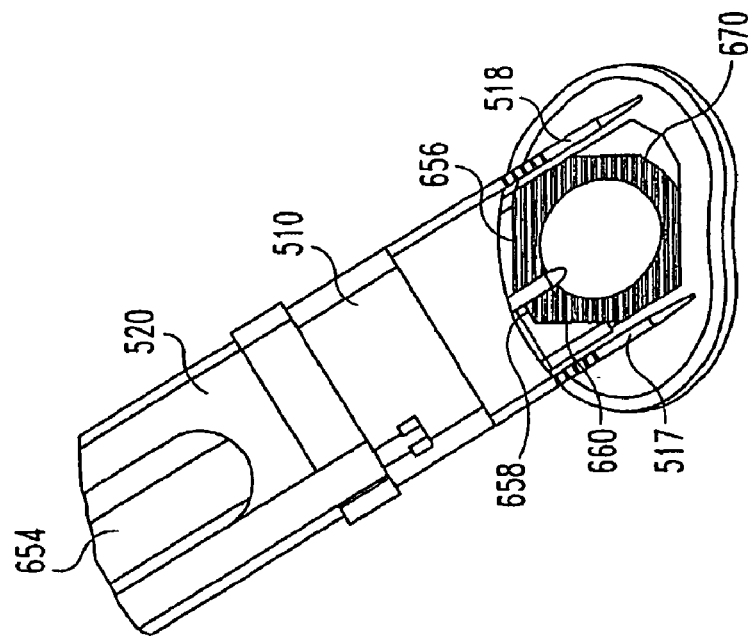
FIG. 34b is an enlarged top view of the a portion of FIG. 34.

An implant inserter such as shown in FIGS. 34 a and b is provided to advance an implant to the disc space. Inserter 650 is substantially as previously described with respect to the inserter of FIG. 19a. Implant inserter 650 includes an outer shaft 654 with an inner shaft disposed therein and having a thumb wheel 652 on the proximal for transmitting rotation force to drive the opposing threaded end of the inner shaft (not shown) into a corresponding opening in implant 670. Implant inserter 650 has modified implant engaging surfaces 656, 658 and 660 adapted to correspond to the surfaces of implant 670 disposed at approximately a 30 degree angle to the approach for grasping the implant. Implant 670 is sized and configured for advancement through guide sleeve 520 and distraction window 510 and placement in the disc space from an oblique anterior approach to the spine.

Figure 36:
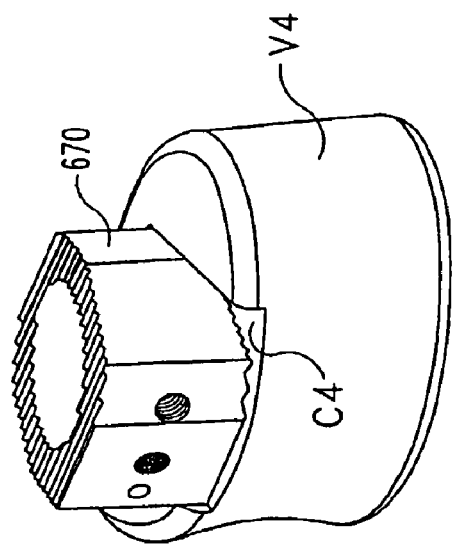
FIG. 36 is an alternative perspective view of the implant and vertebra of FIG. 35.
Figure 37:
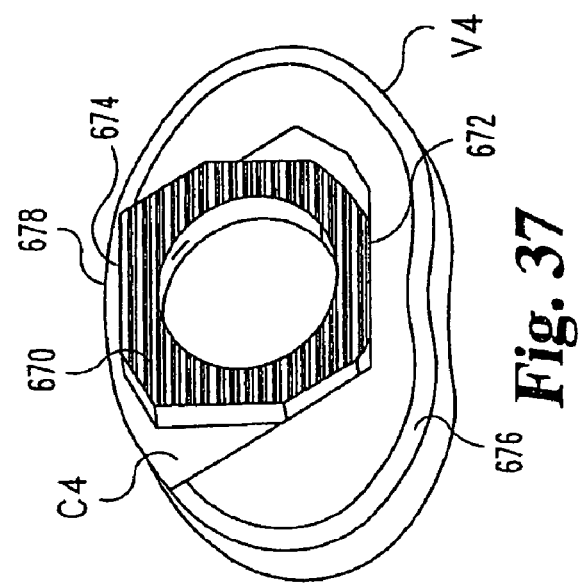
FIG. 37 is another perspective view of the implant and vertebra of FIG. 35.
Figure 35:
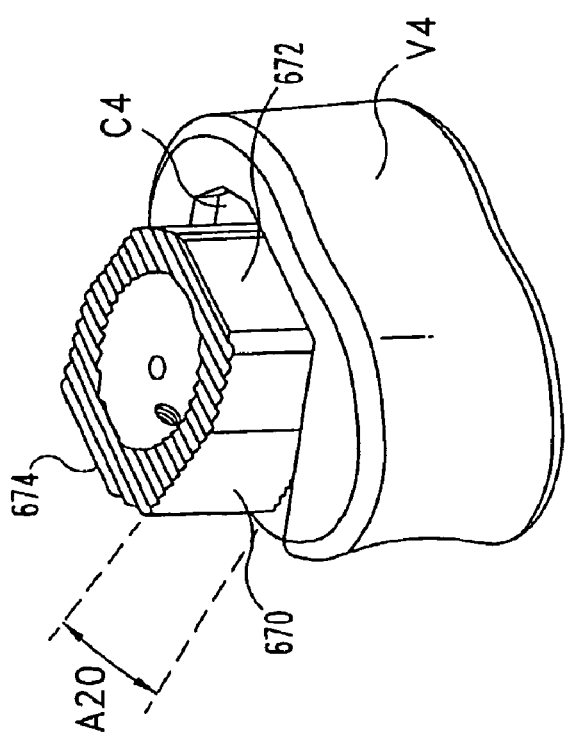
FIG. 35 is a perspective view of a vertebra and implant.

Referring to FIGS. 35 through 37, the final placement of implant 670 in channel or cut C4 in vertebra V4 is shown. Posterior surface 672 is in substantial alignment with posterior portion 676 of vertebra V4. Similarly, anterior surface 674 is in substantial alignment with anterior portion 678 of vertebra V4. Further, the taper between the upper and lower bone engaging surfaces of implant 670, shown by angle A20, extends from the posterior to anterior portion with increasing height. Thus, implant 670 may maintain angulation between adjacent vertebra.

The present invention contemplates a method of guided disc space and endplate preparation from an oblique approach to the spine. The method is initiated by obtaining access to an oblique anterior portion of the spine. This includes well known approaches to the anterior of the spine as well as any required vessel retraction by previously known procedures. Once an oblique portion on the anterior spine adjacent the affected disc space is exposed, all or part of the disc material may be removed. A distractor 408 is then advanced into the disc space from an oblique angle to the spine. For applications where it is desirable to achieve or maintain angulation between adjacent vertebral endplates, distractor 408 may include a desired taper, extending at an angle corresponding to the oblique angle of approach to the spine, to establish the proper angulation. Referring to FIG. 24, after distraction an interconnected distraction window 510 and guide tube 520 are advanced over distractor 408. Distraction window 510 includes distraction flanges have tapering heights, when viewed at the oblique angle of approach to the spine, to maintain the angulation previously established by the distractor. The distraction flanges are advanced into the spine and the bone engaging surfaces of the distraction window are brought into close proximity to the anterior portions of the upper and lower vertebral bodies. With the distraction window properly position in and adjacent the disc space, distractor 408 is removed. Guide tube 520 may also be uncoupled from distraction window 510 and removed. The locking mechanism permits uncoupling from the proximal end of guide tube 520 thus limiting the need for additional vessel retraction adjacent distraction window 510 to permit a surgeon to access a locking mechanism.

The distraction window 510 provides a surgeon with clear access to the disc space and vertebral endplates. As shown in FIG. 40, a depth gauge may be inserted through window 510 to evaluate the depth and area of bony endplate to be removed. Further, distraction window 510 provides a platform for guided preparation of the vertebral body endplates. Referring to FIG. 28, a guide block 550 is slidably received in proximal portion 544 of the distraction window. Insertion portion 552 is configured for a relatively close fit with proximal portion 544, thereby limiting relative movement between the distraction window and guide block. If additional connection between the distraction window and guide block is desired, a locking mechanism may be provided to releasably lock the guide block to the distraction window.

Referring to FIG. 29, a chisel 580 or other non-rotating cutting instrument is inserted into blade guide 554 of the guide block. In a preferred embodiment intended for preparing endplates with a desired angulation, the blade guide includes a compound angular relation to the distraction window. Specifically, blade guide includes an oblique side-to-side angle as well as an oblique front-to-back angle. In a further preferred aspect, the cutting blade includes a guiding ridge 610 adapted to be received within guiding channel 570 thereby providing additional control over the blade advancement.

The cutting blade is advanced through the upper blade guide and a corresponding portion of vertebral endplate is removed. The debris from the cutting procedure may be removed with the guide block still in place or the guide block may be disengaged from the distraction window and the debris removed. Once the debris is removed, the endplate may be visually inspected. If the user desires the removal of additional endplate bone, a guide block permitting an incrementally greater amount of bone removal, typically in 1 mm increments, may be substituted for guide block 550 and the cutting blade reinserted. Once the upper endplate is satisfactorily prepared, a lower guide block 595 may be inserted into distraction window 510. A cutting blade cooperable with the lower guide block is inserted into blade guide 597 and utilized to similarly prepare the lower endplate.

Once the upper and lower vertebral endplates have been properly prepared with cuts or channels adapted to receive an implant, the guide blocks are removed from the distraction window. Preferably, guide tube 520 is reconnected to distraction window 510. An implant is interconnected with an implant inserter and the implant is positioned through the guide tube and distraction window into the disc space. Despite the fact that the implant has been inserted from an oblique angle to the spine, the guided disc space preparation permits placement of tapered implant in the proper orientation in the disc space. The final implant placement shown in FIGS. 35 through 37 is comparable to the implant placement shown in FIGS. 20a and b accomplished by a direct anterior approach to the spine. Thus, the present method of implant placement provides a new guided approach to the spine that may be particularly useful where patient anatomy makes direct anterior or lateral approaches to the spine difficult and/or dangerous to patient health.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A medical instrument for preparation of a disc space between adjacent vertebrae of a patient, comprising:
    a distractor including a distraction head adapted to distract the adjacent vertebrae from an oblique approach with respect to a sagittal plane of the patient, said distraction head including opposite first and second side walls extending along a longitudinal axis to a leading portion, said leading portion of said distraction head further including a first leading edge extending from said first side wall and a second angled leading edge extending from said second side wall toward said first leading edge, said second leading edge forming an oblique angle with respect to said first leading edge, wherein said first leading edge and said second leading edge each have adjoining upper and lower tapered surfaces that extend away from one another in a direction away from respective ones of said first and second leading edges, wherein:
    said upper and lower tapered surfaces respectively adjoin upper and lower distraction surfaces, and said upper and lower distraction surfaces extend between said first and second side walls;
    said upper distraction surface terminates in an upper bone engaging surface, and said lower distraction surface terminates in a lower bone engaging surface; and
    said upper and lower bone engaging surfaces project outwardly in opposite directions from respective ones of said upper and lower distraction surfaces and are each defined by a concave arcuate surface facing toward said leading portion with said concave curvature extending away from said leading portion, said concave arcuate surfaces each defined by an off-centered radius of curvature, said upper and lower bone engaging surfaces each including a leading end adjacent said first side wall and an opposite trailing end adjacent said second side wall, said leading end extending more distally toward said first leading edge than said trailing end.

2. The instrument of claim 1, wherein said distractor further includes a shaft coupled to said distraction head, wherein said shaft has a tool engaging end adapted to engage a tool.

3. The instrument of claim 2, wherein said distraction head has an offset slot defined therein, wherein said slot extends through said leading portion to open at said first and second leading edges and said slot is off center with respect to a centerline of said distraction head that parallelly extends between said first and second side walls so that said slot is spaced a first distance from said first side wall and a second distance from said second side wall, said first distance being greater than said second distance.

4. The instrument of claim 3, further comprising a guiding fin having a height greater than corresponding portions of said distraction head provided in said slot, wherein said fin is adapted to cut a guide channel in the vertebrae to maintain proper orientation of said distraction head during insertion.

5. A medical instrument for preparation of a disc space between adjacent vertebrae of a patient, comprising:
    a distractor including a distraction head adapted to distract the adjacent vertebrae from an oblique approach with respect to a sagittal plane of the patient, said distraction head including opposite first and second side walls extending along a longitudinal axis to a leading portion, said leading portion of said distraction head further including a first leading edge extending from said first side wall and a second angled leading edge extending from said second side wall toward said first leading edge, said second leading edge forming an oblique angle with respect to said first leading edge, wherein said first leading edge and said second leading edge each have adjoining upper and lower tapered surfaces that extend away from one another in a direction away from respective ones of said first and second leading edges, further comprising an offset slot defined in said distraction head and a guiding fin having a height greater than corresponding portions of said distraction head provided in said slot, wherein said fin is adapted to cut a guide channel in the vertebrae to maintain proper orientation of said distraction head during insertion.

6. The instrument of claim 1, further comprising a distraction window having a working channel defined therein, said distractor being provided in said working channel, said distraction window being adapted to engage the adjacent vertebrae from the oblique approach with respect to the sagital plane of the patient.

7. The instrument of claim 6, further comprising a guide tube having a locking mechanism coupled to said distraction window.

8. The instrument of claim 1, wherein said upper and lower tapered surfaces extending from said second leading edge are formed in a plane extending at said oblique angle with respect to a plane in which said upper and lower tapered surfaces extending from said first leading edge are formed.

9. The instrument of claim 1, wherein said oblique angle is about 30 degrees.

10. The instrument of claim 1, wherein said distraction head has an offset slot defined therein, wherein said slot extends through said leading portion to open at said first and second leading edges and said slot is off center with respect to a centerline of said distraction head that parallelly extends between said first and second side walls so that said slot is spaced a first distance from said first side wall and a second distance from said second side wall, said first distance being greater than said second distance.

11. A medical instrument for preparation of a disc space between adjacent vertebrae of a patient, comprising:
a distractor including a distraction head adapted to distract the adjacent vertebrae from an oblique approach with respect to a sagittal plane of the patient, said distraction head including opposite first and second side walls extending along a longitudinal axis to a leading portion, said leading portion of said distraction head further including a first leading edge extending from said first side wall and a second angled leading edge extending from said second side wall toward said first leading edge, said second leading edge forming an oblique angle with respect to said first leading edge, wherein said first leading edge and said second leading edge each have adjoining upper and lower tapered surfaces that extend away from one another in a direction away from respective ones of said first and second leading edges, wherein:
said upper and lower tapered surfaces respectively adjoin upper and lower distraction surfaces;
said upper and lower distraction surfaces extend between said first and second side walls and terminate at respective ones of upper and lower bone engaging surfaces;
said upper and lower bone engaging surfaces project outwardly in opposite directions from respective ones of said upper and lower distraction surfaces and each includes a leading end adjacent said first side wall and an opposite trailing end adjacent said second side wall, said leading end extending more distally in a direction toward said first leading edge than said trailing end; and
said upper and lower bone engaging surfaces are concavely curved between said leading end and said tailing end, said concavely curved bone engaging surfaces facing said leading portion with said concavely curved bone engaging surfaces being concavely curved away from said leading portion.

12. The instrument of claim 11, wherein said distraction head includes a centering block extending proximally from said bone engaging surfaces toward a rear of said distraction head, said centering block including opposite inclined upper and lower surfaces and opposite inclined side surfaces.

13. The instrument of claim 11, wherein said distraction head has an offset slot defined therein, wherein said slot extends through said leading portion to open at said first and second leading edges and said slot is off center with respect to a centerline of said distraction head that parallelly extends between said first and second side walls so that said slot is spaced a first distance from said first side wall and a second distance from said second side wall, said first distance being greater than said second distance.

* * * * *